*(12)* United States Patent
Procter et al.

(10) Patent No.: US 12,251,490 B2
(45) Date of Patent: *Mar. 18, 2025

(54) COMPOSITION OF ALPHA-TCP, SILICATE AND PHOSPHORYLATED AMINO ACID

(71) Applicant: GPBIO LTD., Limerick (IE)

(72) Inventors: Philip Procter, Divonne les Bains (FR); Håkan Engqvist, Uppsala (SE); Michael Pujari-Palmer, Uppsala (SE); Gerard Insley, Limerick (IE)

(73) Assignee: BIOMIMETIC INNOVATIONS LIMITED (IE)

( * ) Notice: Subject to any disclaimer, the term of this patent is extended or adjusted under 35 U.S.C. 154(b) by 887 days.

This patent is subject to a terminal disclaimer.

(21) Appl. No.: 16/337,355

(22) PCT Filed: Sep. 27, 2017

(86) PCT No.: PCT/EP2017/074551
§ 371 (c)(1),
(2) Date: Mar. 27, 2019

(87) PCT Pub. No.: WO2018/060287
PCT Pub. Date: Apr. 5, 2018

(65) Prior Publication Data
US 2020/0038545 A1    Feb. 6, 2020

(30) Foreign Application Priority Data

Sep. 27, 2016 (SE) .................... 1651271-7

(51) Int. Cl.
| | | |
|---|---|---|
| *A61L 24/02* | (2006.01) | |
| *A61B 17/00* | (2006.01) | |
| *A61K 6/30* | (2020.01) | |
| *A61L 24/00* | (2006.01) | |
| *A61L 27/12* | (2006.01) | |
| *A61L 27/52* | (2006.01) | |

(52) U.S. Cl.
CPC ........ *A61L 24/02* (2013.01); *A61B 17/00491* (2013.01); *A61K 6/30* (2020.01); *A61L 24/0031* (2013.01); *A61L 27/12* (2013.01); *A61L 27/52* (2013.01); *A61B 2017/00495* (2013.01); *A61B 2017/005* (2013.01); *A61L 2400/06* (2013.01); *A61L 2430/34* (2013.01)

(58) Field of Classification Search
CPC ...... A61L 24/02; A61L 24/0031; A61L 27/12; A61L 27/52; A61L 2400/06; A61L 2430/34; A61L 27/025; A61L 2430/02; A61L 2430/12; A61L 27/02; A61L 2430/00; A61B 17/00491; A61B 2017/00495; A61B 2017/005; A61K 6/30; A61K 47/02; A61K 33/42; C09J 1/02; C09J 11/04

See application file for complete search history.

(56) References Cited

U.S. PATENT DOCUMENTS

| | | |
|---|---|---|
| 6,533,821 B1 | 3/2003 | Lally |
| 8,105,086 B2 | 1/2012 | Asgary |
| 11,247,941 B2 | 2/2022 | Hess et al. |
| 11,638,777 B2 | 5/2023 | Hess et al. |
| 2005/0217538 A1 | 10/2005 | Reinstorf et al. |
| 2009/0087390 A1 | 4/2009 | Modi |
| 2010/0121459 A1 | 5/2010 | Garigapati et al. |
| 2011/0277931 A1 | 11/2011 | Garigapati et al. |
| 2012/0288446 A1 | 11/2012 | Garigapati et al. |
| 2013/0122057 A1 | 5/2013 | Garigapati et al. |
| 2020/0030483 A1 | 1/2020 | Procter |

FOREIGN PATENT DOCUMENTS

| | | |
|---|---|---|
| CN | 101014376 A | 8/2007 |
| WO | WO 2006-041365 | 4/2006 |
| WO | WO 2016/196371 | 12/2016 |
| WO | WO 2018/060287 | 4/2018 |

OTHER PUBLICATIONS

Office Action issued for CN 201780059294.7 dated Apr. 6, 2021 (English translation) 21 pgs.
Correa et al., "α-Tricalcium phosphate cements modified with β-dicalcium silicate and tricalcium aluminate: Physicochemical characterization, in vitro bioactivity and cytotoxicity", J. Biomedical Materials Research B: Applied Biomaterials, Jan. 2015, vol. 103B, Issue 1:72-83.
Dorozhkin, "Calcium orthophosphate-based biocomposites and hybrid biomaterials", J Mater Sci (2009) 44:2343-2387.
International Search report for PCT/EP2017/074551, dated Dec. 13, 2017, 3 pages.
Morejon-Alonso et al., "Effects of Silica Addition on the Chemical, Mechanical and Biological Properties of a New α-Tricalcium Phosphate/Tricalcium Silicate Cement", Materials Research, 2011, 14(4): 475-482.
Mostafa et al., "Injectable Bone Cement Based on Calcium Silicate and Calcium Phosphate", Int. J. Chem. Sci.: 13(1), 2015: 80-96.

(Continued)

*Primary Examiner* — Jessica Worsham
(74) *Attorney, Agent, or Firm* — Quarles & Brady LLP

(57) ABSTRACT

The present invention relates to an aqueous composition comprising an aqueous solution, α-TCP, a silicate compound and a phosphorylated amino acid. The composition has improved mechanical strength and is easily applied and may be used as a tissue adhesive, implant or a filler.

23 Claims, 24 Drawing Sheets

(56) References Cited

OTHER PUBLICATIONS

Motisuke et al., "Apatite bone cement reinforced with calcium silicate fibers", J. Mater Sci: Mater Med (2014) 25:2357-2363.
Schneiders et al., "Effect of modification of hydroxyapatite/collagen composites with sodium citrate, phosphoserine, phosphoserine/RGD-peptide and calcium carbonate on bone remodeling", Bone 40 (2007): 1048-1059.
Office Action mailed Jul. 12, 2023 with respect to U.S. Appl. No. 16/337,350.
Coppey, et al., "Early Complications From the Use of Calcium Phosphate Paste in Mandibular Lengthening Surgery. A Retrospective Study" J Oral Maxillofac Surg. 2017;75(6):1274.e1-1274.e10. doi:10.1016/j.joms.2017.01.017.
Duan, et al., "Applications of Bioadhesives: A Mini Review", Frontiers in Bioengineering and Biotechnology, Sep. 2021 Vol. 9:7; 1-12., Seot. 2021, 1-12.
Ge, et al., "Review: Recent Advances in Tissue Adhesives for Clinical Medicine", Polymers, (2020) 12:939 p. 1-22.
Hexarmor, "Concrete irritation, burns, and dermatitis", Retrieved Aug. 26, 2022, from https://www.hexarmor.com/posts/concrete-irritation-burns-and-dermatitis.
International Search Report, for PCT/EP2017/074553, dated Dec. 13, 2017, 3 pages.
Li, et al., "Ability of Obturation Materials to Improve the Seal of the Root Canal System—a Review", Acta Biomater. (2014) 10(3): pp. 1050-1063.
NPL, search for "phosphoserine" in PubChem; downloaded May 1, 2020.
Office Action, issued for U.S. Appl. No. 16/337,350 dated May 7, 2020, 52 pages.
Office Action, issued for U.S. Appl. No. 16/337,350 dated Nov. 4, 2020, 14 pages.
Office Action, issued for U.S. Appl. No. 16/337,350 dated Jul. 26, 2021, 27 pages.
Office Action, issued for U.S. Appl. No. 16/337,350 dated Sep. 10, 2021, 14 pages.
Office Action, issued for U.S. Appl. No. 16/337,350 dated Apr. 1, 2022, 16 pages.
Office Action, issued for U.S. Appl. No. 16/337,350 dated Nov. 30, 2022, 33 pages.
Van Loghem, et al., "Managing intravascular complications following treatment with calcium hydroxylapatite: An expert consensus" J Cosmet Dermatol. 2020;19(11):2845-2858. doi: 10.1111/jocd.13353.

| Material | Cortical bond strength |
|---|---|
| Cortical bone | 123.2 |
| Steel | 112.0 |
| Titanium | 81.4 |
| PLA | 43.4 |

| Material | Reaction |
|---|---|
| aTCP | Adhesive |
| Octacalcium Phosphate | No Reaction |
| Hydroxyapatite | No Reaction |
| Brushite | No Reaction |
| Ca-Silicate | No Reaction |
| Ca-Disilicate | Adhesive |
| Ca-Trisilicate | Adhesive |
| Mg-Silicate (Talc) | No Reaction |
| Al-Silicate (Kaolin) | No Reaction |
| Ca-Aluminate | No Reaction |
| CaS Hemihydrate | No Reaction |
| a-CaS Hemihydrate | No Reaction |
| b-CaS Hemihydrate | No Reaction |
| CaS Dihydrate | No Reaction |
| a-CaS Anhydrous | No Reaction |

Fig. 15

COMPOSITION OF ALPHA-TCP, SILICATE AND PHOSPHORYLATED AMINO ACID

CROSS-REFERENCE TO RELATED APPLICATION

This application claims priority to and is a 35 U.S.C. § 371 national phase application of PCT/EP2017/074551 (WO2018/060287), filed on Sep. 27, 2017 entitled "COMPOSITION OF α-TCP, SILICATE AND PHOSPHORYLATED AMINO ACID", which application claims priority to and the benefit of Sweden Patent Application No. 1651271-7, filed Sep. 27, 2016, the disclosures of which are incorporated herein by reference in their entirety.

FIELD OF THE INVENTION

The present invention relates to a composition of α-TCP, a silicate compound and a phosphorylated amino acid where the composition may be used as an adhesive or an implant. The invention further relates to a method of treating tissue and a kit.

BACKGROUND

Calcium phosphates (CaP) and in particular hydroxyapatite ($Ca_{10}(PO_4)_6(OH)_2$, HA), is a mineral that is widely used in medical applications due to its similarity to the mineral components of bone and teeth and its biocompatibility. Furthermore hydroxyapatite is non-toxic, biocompatible and bioactive. This means that hydroxyapatite is not harmful and not recognized as a foreign body and on the other hand that it may have positive effects on remodelling of bone. Hence hydroxyapatite has been widely used in bone repair and as drug/gene delivery vehicle, catalyst, ion adsorption/exchange agent, photoelectric regent and so on. Resorbable nanoparticles (i.e. particles that can be dissolved in vivo) are of special interest for a number of applications, e.g. bone void fillers, drug delivery vehicle, desensitization of dentin tubuli and so on.

The field of biomaterials includes fixation of implants to tissues as well as tissue repair. The limited mechanical strength of implants in combination adhesives has remained an issue within the field of implants and biomaterials. The repair of soft tissues or internal organs with adhesives has also been broadly unsuccessful.

US2012288446 (US'446) discloses an adhesive comprising a multivalent metal compound, a compound comprising a phosphoserine oligomer or a phosphoserine capped polymer wherein the latter compound is present at 10-90 wt %. US'446 discloses experimental data using tetra calcium phosphate (TTCP) as the multivalent metal compound and phosphoserine-ethyleneglycol-diglycidyl-phosphoserine for example and obtains adhesive strength of up to 3.76 MPa when adhered to bone.

US20130122057 (US'057) discloses a bone restorative composition comprising amino acid phosphate species, a multivalent metal compound and a bioactive glass material containing ionic functional groups. US'057 disclose examples using a composing comprising TTCP as the multivalent metal compound and phosphoserine together with various amounts of Combeite Bioactive glass and water and adhere it to bone. The shear strengths obtained varied between 0.75-2.13 MPa.

U.S. Pat. No. 8,765,189 (US'189) teaches an adhesive composition comprising a multivalent metal compound and a phosphoserine like compound in an amount of 10-90 wt %. US'189 disclose an adhesion shear strength to cortical bone after 5 minutes of 130-890 kPa when using TTCP as the multivalent metal compound and various phosphorylated compounds and 650 kPa when using α-TCP and phosphoserine.

Even though there are several tissue adhesives available today on the market none of them are ideal sealants or even adhesives. Cyanoacrylates have shown good adhesion but have shown inflammatory response during degradation. Fibrin glues have low adhesive strength but are more biocompatible. Other adhesives struggle with high costs and long curing times or the lack of tailoring the curing time dependent on the tissue and the situation. Soft tissue adhesive usually contain fibrin or gelatin other various polysaccharides.

Still the adhesives cannot withstand any major shear forces and none of them have shown or implied that they would work also on soft tissues. There is therefore a need for a composition that may be used as a tissue adhesive especially for soft tissues which also provides high shear strength.

SUMMARY OF THE INVENTION

The aim of the present invention is to overcome the drawbacks of the prior art. Therefore in a first aspect the present invention relates to an aqueous composition comprising an aqueous solution, a silicate compound, α-TCP and a phosphorylated amino acid; wherein the amount of phosphorylated amino acid is 15-90 wt % of the solid content and wherein the weight ratio of the silicate compound and α-TCP is 1:0.001-100.

In a second aspect the present invention relates to a biological tissue adhesive.

In a third aspect the present invention relates to a bone filler.

In a fourth aspect the present invention relates to a dental implant.

In a fifth aspect the present invention relates to the use of the aqueous composition adhering soft tissue to hard or soft tissue.

In a sixth aspect the present invention relates to the use of the aqueous composition for adhering an implant or a scaffold to a tissue wherein the implant or scaffold is made of metal, polymeric material, ceramic or tissue-derived products such as collagen, matrigel, autologous blood, platelet rich plasma or demineralized bone.

In an eight aspect the present invention relates to the use of the aqueous composition for strengthening sealed or repaired tissue.

In a ninth aspect the present invention relates to a method of adhering a first tissue to a second surface using the tissue adhesive according to the present invention comprising:
a. applying the tissue adhesive according to the present invention to the first tissue or to the second surface and optionally leave it for a suitable period of time;
b. bringing the first tissue and the second surface into contact with each other;
c. optionally applying a pressure on the first and second tissue for a suitable period of time; and
d. letting the tissue adhesive cure.

In a tenth aspect the present invention relates to a kit for preparing the composition according to the present invention comprising at least two containers wherein any one container in the kit can contain any of an aqueous solution, the phosphorylated amino acid, the silicate compound or the α-TCP or a combination thereof, with the proviso that both the phosphorylated amino acid and the α-TCP cannot be present in the same container as the aqueous solution; and wherein the amount of aqueous solution, phosphorylated amino acid, silicate compound and α-TCP in the containers is such that when mixed the composition according to the present invention is obtained.

In an eleventh aspect the present invention relates to a syringe comprising at least two compartments wherein any one compartment in the syringe can contain any of an aqueous solution, the phosphorylated amino acid, the silicate compound or the α-TCP or a combination thereof, with the proviso that both the phosphorylated amino acid and the α-TCP cannot be present in the same compartment as the aqueous solution; wherein the amount of aqueous solution, phosphorylated amino acid, silicate compound and α-TCP in the compartments is such that when mixed the composition according to the present invention is obtained; and wherein the syringe further comprises a mixing device configured to mix the components of the at least two compartments.

All the embodiments presented herein relates to all the aspects of the present invention.

BRIEF DESCRIPTION OF THE FIGURES

FIG. 15. Adhesion strength of cortical bone to commonly used biomaterials, with Portland grey cement (mixture of di- and tricalcium silicates) (hard tissue). Reactivity of various ionic salts with phosphoserine, tested over the range of 20-80% phosphoserine (wt %).

DETAILED DESCRIPTION OF THE INVENTION

In the present application the word "aqueous solution" also encompasses water and water of any purity. The water may be but is not limited to tap water, distilled water or deionized water. The aqueous solution may also be a buffer such as PBS or any suitable saline buffer.

The Composition

The composition according to the present invention is an aqueous composition comprising an aqueous solution, α-TCP, a silicate compound and a phosphorylated amino acid.

The present inventors have found that this composition provides improved mechanical strength and easy handling. Also the composition has shown to be suitable for adhering soft tissue to either hard tissue or a synthetic implant or scaffold but also soft tissue to soft tissue. The latter is a long felt need within the field and the present invention not only facilitates adherence of soft tissue to soft tissue but the mechanical strength of the adhesive is unexpectedly high.

Surprisingly the present inventors found that the improvements of the present composition were only true for α-TCP but not for β-TCP. The α-TCP may be used in any form or shape but is preferably in form of a powder having a mean particle size of 5-5000 nm such as 20 nm or larger, 50 nm or larger, 100 nm or larger, or 300 nm or larger, or 500 nm or larger, or 800 nm or larger, or 3000 nm or smaller, or 1500 nm or smaller, or 1000 nm or smaller. The particles may be spherical or in the shape of flakes.

The silicate compound may be used in any form or shape but is preferably in form of a powder having a mean particle size of 5-5000 nm such as 20 nm or larger, 50 nm or larger, 100 nm or larger, or 300 nm or larger, or 500 nm or larger, or 800 nm or larger, or 3000 nm or smaller, or 1500 nm or smaller, or 1000 nm or smaller. Preferably the sizes of the α-TCP and the silicate compounds are similar in order to avoid settling.

Figure 10:
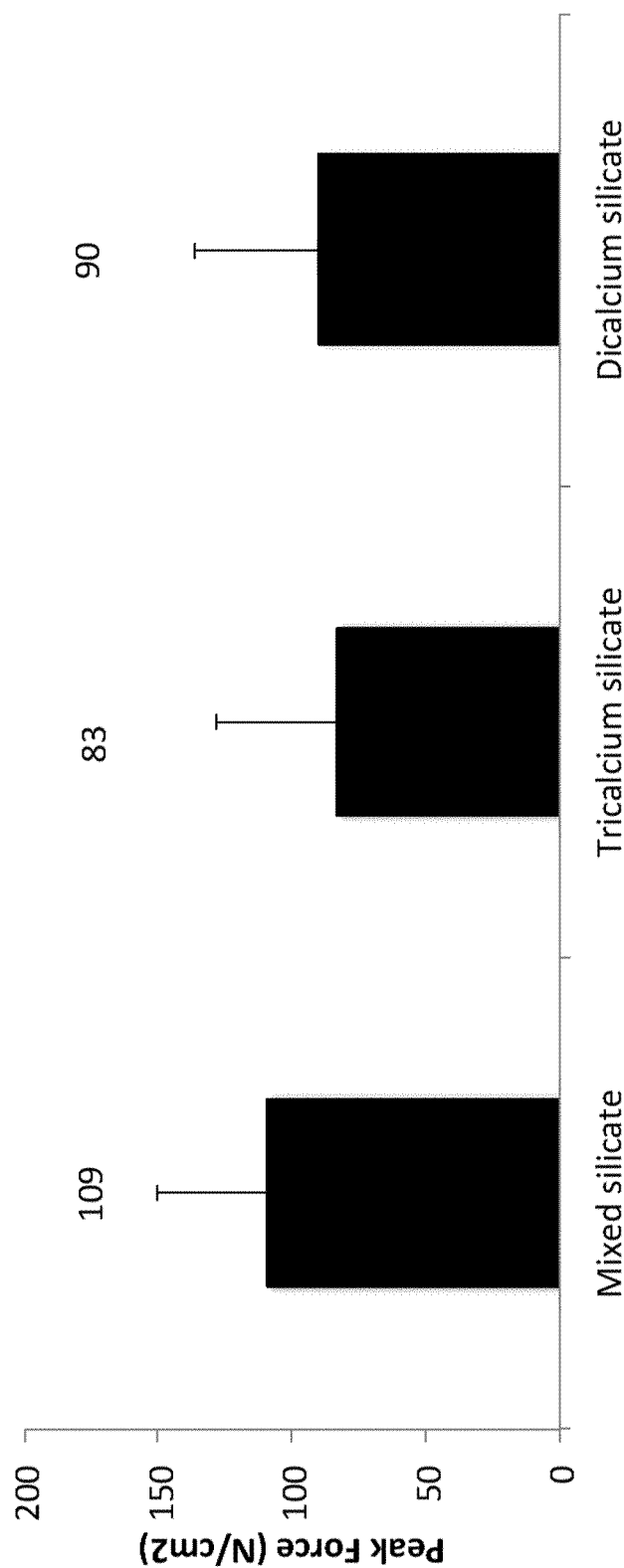
FIG. 10. Adhesion strength (shear) of unmixed and Portland grey cement (hard tissue). Cortical shear strength (24 hours, 100% humidity, 21° C.) with mixed calcium silicates, tricalcium silicate or dicalcium silicate.

Without being bound by theory it is believed that the silicate compound in combination with the α-TCP increases the mechanical strength of the formed material. The silicate compound also makes it easier to tailor the curing time as there are multiple forms of calcium silicate, each with different reaction speeds and handling properties. For example, the tricalcium form of calcium silicate reacts very quickly, while the dicalcium form reacts much slower and is reported to contribute more to long term curing strength. The monocalcium silicate (metasilicate) reacts so slowly that no reaction is easily discerned. The handling properties also differ for each form. Mixtures of the many silicate forms can produce optimal handling and reaction speeds that may be difficult or impossible to obtain using a single silicate phase. Alternatively, adding more aqueous solution can slow the reaction, partially due to changes in solubility. FIG. 10 shows the shear strength for different calcium silicates.

The silicate compound may be any suitable compound comprising a silicate i.e. an anionic silicon compound. The silicon compound may be an oxide such as $[SiO_4]^{2-}$ or $[Si_2O_7]^{6-}$ or quartz, feldspars, zeolites, micas, pyroxene etc. In one embodiment the silicate compound is selected from calcium silicate, sodium silicate and aluminum silicate, magnesium silicate, strontium silicate; zirconium silicate; or a mixture of di- and tri-calcium silicate preferably calcium silicate. The silicates may be in the form of a cement such as Portland grey cement or Portland white cement. A mixture of di- and tricalcium silicate may comprise between 0-100 wt % of dicalcium silicate and between 0-100 wt % of tricalcium silicate such as 30-70 wt % of di-calcium silicate and 30-70 wt % of tri-calcium silicate. Tests with different silicate compounds are disclosed in FIG. 10. FIG. 15 shows that only α-TCP and the di- and the tri-silicates show any adhesive reactions together with phosphoserine.

The amount of silicate compound and α-TCP may be 10-85 wt % of the solid content of the composition. In one embodiment the amount is 20-50 wt % such as 25-40 wt %. In another embodiment the amount is 50-85 wt % such as 60-80 wt %. The amount is dependent on the application and the tissue. The weight ratio of the silicate compound and the α-TCP should be 1:0.001-100 (silicate compound:α-TCP). The present inventors have found that the optimum weight ratio is dependent on the tissue or the application. In one embodiment the weight ratio is 1:0.05-15. In another embodiment the weight ratio is 1:0.05-0.4 such as 1:0.1-0.3. In yet another embodiment the weight ratio is 1:5-20, such as 1:9-15. In another embodiment the weight ratio is 1:1-4 such as 1:1.5-3.5. In yet another embodiment the weight ratio is 1:15-25.

Phosphorylation is the addition of a phosphate group ($PO_4^{3-}$) to an amino acid or any other molecule. Phosphorylated amino acids according to the present invention may for example be phosphorylated serine, threonine or tyrosine but could also be other amino acids. In one embodiment the phosphorylated amino acid is phosphorylated serine also known as phosphoserine (pSer). The phosphorylated amino acids according to the present invention may be functionalized or non-functionalized. The phosphorylated amino acids according to the present invention may be monomers or dimers or trimers.

It is believed that the phosphorylated amino acid acts as a curing agent providing improved mechanical strength to the composition. The amount of phosphorylated amino acid should be 15-90 wt % of the solid content of the composition. In order to balance the different properties of the inherent components of the composition the amount of phosphorylated amino acid may depend on the ratio between the silicate compound and the α-TCP. In one embodiment a preferred amount of phosphorylated amino acid is 15-50 wt % such as 22 wt % or more, or 25 wt % or more, or 30 wt % or more, but 45 wt % or less, or 40 wt % or less, or 35 wt % or less, for example 20-40 wt % or 22-35 wt %. In one embodiment this preferred amount of phosphorylated amino acid is used when the ratio of silicate compound and α-TCP is 1:5-15. In one embodiment the amount is 22-30 wt %. In another embodiment a preferred amount is 30-75 wt % such as 35 wt % or more, or 40 wt % or more, or 45 wt % or more but 65 wt % or less, or 60 wt % or less, or 55 wt % or less. This latter preferred amount of phosphorylated amino acid may be used when the ratio of silicate compound and α-TCP is 1:0.05-0.4.

Figure 7:
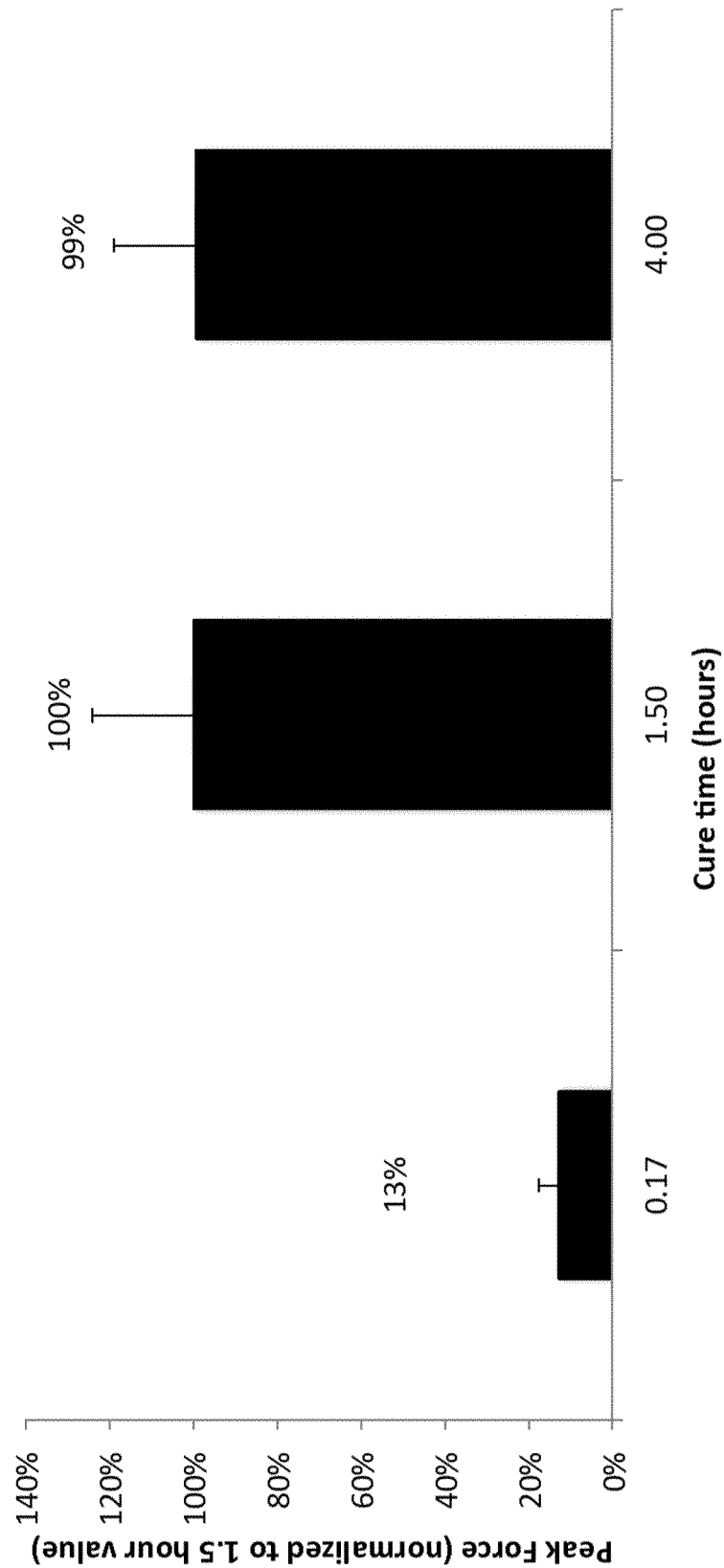
FIG. 7. Curing time for mixed silicate formulation B (56 wt % Pser, 35 wt % aTCP and 9 wt % Portland white cement (solid content %) with 17% liquid (total wt %)) (soft tissue). Skin shear curing time (cured in 100% humidity at 21° C.), force normalized to the strength at 1.5 hours.
Figure 8:
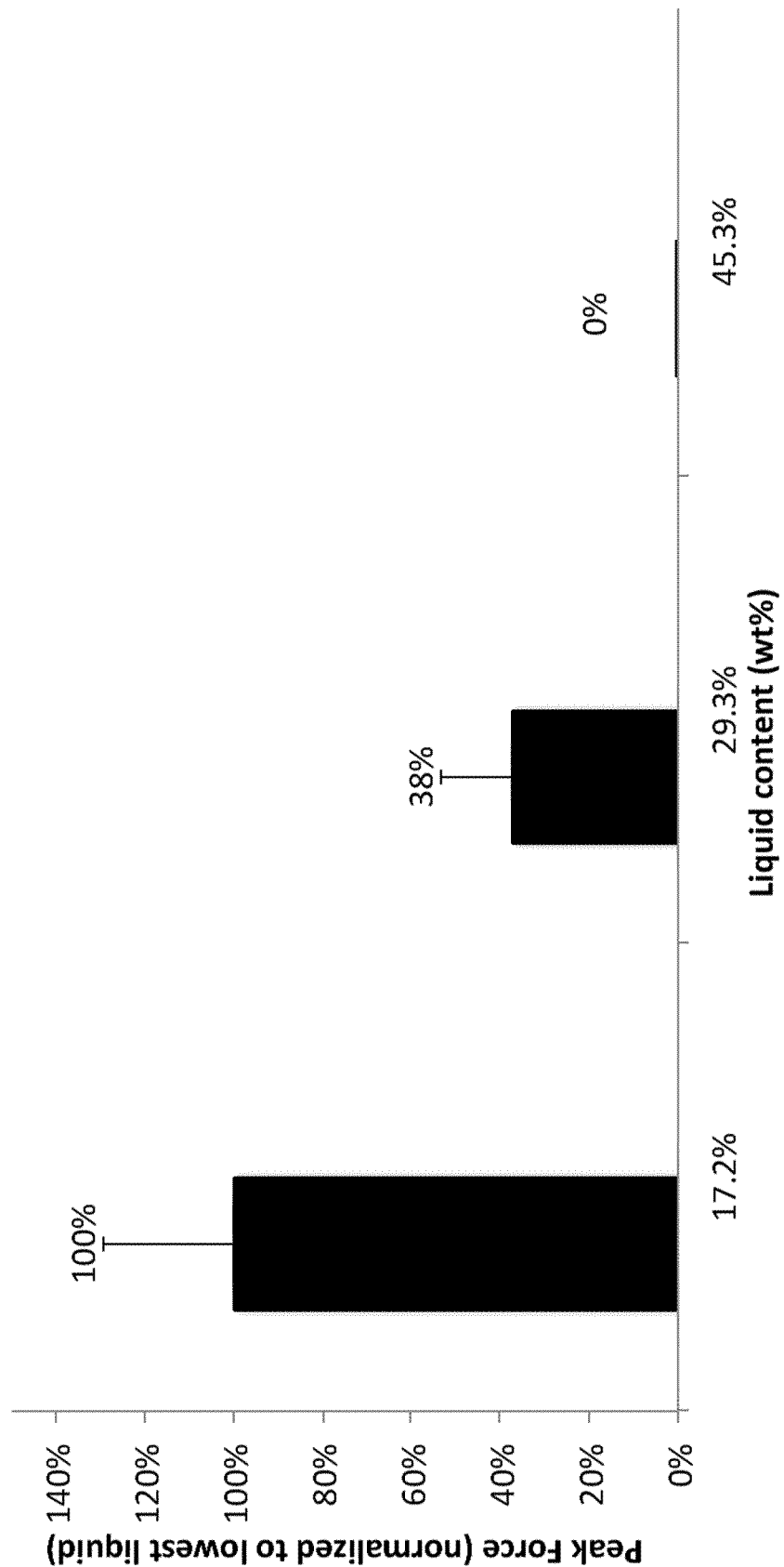
FIG. 8. Adhesive strength by water content, Portland grey cement (mixture of di- and tricalcium silicates where the major elements are $SiO_2$ (19.5%), $Al_2O_3$ (5.2%) and CaO (63.9%)) (hard tissue). Cortical shear strength with increasing water content (cured in distilled water at 21° C.), force normalized to the strength at lowest water content.

The composition may comprise any suitable amount of aqueous solution for example 5-95 wt % of the total weight of the composition, such as 10 wt % or more, or 15 wt % or more, or 20 wt % or more, or 90 wt % or less, or 80 wt % or less, or 70 wt % or less, or 60 wt % or less, or 50 wt % or less, or 40 wt % or less, or 30 wt % or less, or 25 wt % or less. The effect of the amount of water is shown in FIGS. 7 and 8. The water may be distilled or deionized water or any water of high purity but tap water may also be used, FIG. 13. The aqueous solution may also be in the form of a hydrogel such as hyaluronic acid, polyvinyl alcohol, chitosan, collagen or a combination thereof. By using a hydrogel as the aqueous solution the composition may more easily remain at the wanted location during curing.

An advantage of the present invention is that the curing time may be tailored so that it cures at the right moment. This is dependent on the application. Sometimes the composition should cure very rapidly and sometimes the composition should be mixed or shaped for a while and when applied it might need some adjustment and therefore the curing should be postponed.

Figure 4:
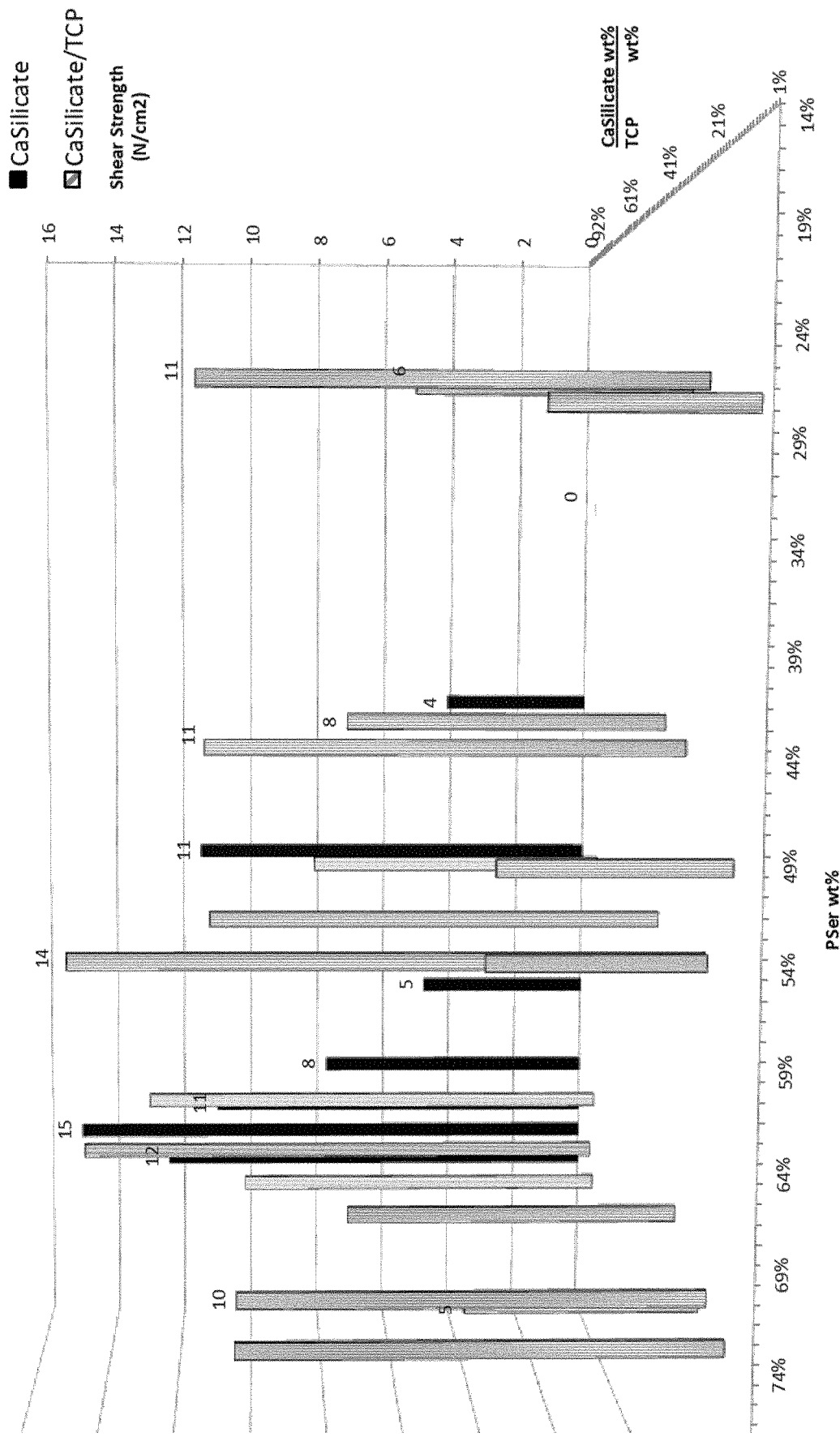
FIG. 4. Chemical composition chart (soft tissue). Skin lap shear (soft tissue-to-soft tissue adhesion) after 1.5 hours in 100% humidity, 37° C.

For soft tissue a composition comprising an aqueous solution, α-TCP, a silicate compound and a phosphorylated amino acid wherein the amount of aqueous solution is 10-30 wt % of the total weight of the composition may be used. The weight ratio between the silicate compound and the α-TCP and is 1:0.1-10 in the composition and wherein the amount of phosphorylated amino acid is 50-85 wt % of the solid content. This composition provides good adhesion to soft tissue as seen in FIG. 4.

For hard tissue a composition comprising an aqueous solution, α-TCP, a silicate compound and a phosphorylated amino acid wherein the amount of aqueous solution is 10-30 wt % of the total weight of the composition may be used. The weight ratio between the silicate compound and the α-TCP is 1:1-50 and wherein the amount of phosphorylated amino acid is 20-50 wt % of the solid content. This composition provides good adhesion to hard tissue as seen in FIG. 2, FIGS. 3A-D and Table 2. Based on criteria such as final adhesive strength (shear strength), workability and curing time in bone adhesion applications, particularly good results were obtained for compositions comprising:

28-39 wt % phosphorylated amino acid (phosphoserine) and 61-72 wt % silicate and α-TCP, and wherein the weight ratio between silicate compound and α-TCP was 82-92 wt % (region denoted A in FIG. 2, FIGS. 3A-D and Table 2);

40-48 wt % phosphorylated amino acid (phosphoserine) and 52-60 wt % silicate and α-TCP, and wherein the weight ratio was 28-33 wt % silicate (region denoted B in FIG. 2, FIGS. 3A-D and Table 2);

22-28 wt % phosphorylated amino acid (phosphoserine) and 72-78 wt % silicate and α-TCP, and wherein the weight ratio was 28-33 wt % silicate (region denoted C in FIG. 2, FIGS. 3A-D and Table 2);

23-29% phosphorylated amino acid (phosphoserine) and 71-77 wt % silicate and α-TCP, and wherein the weight ratio was 2-6 wt % silicate (region denoted D in FIG. 2, FIGS. 3A-D and Table 2).

Peak shear values were obtained for:
A: 31.6% Pser, 88.6% Silicate/TCP ratio
B: 44.7% Pser, 29.6% Silicate/TCP ratio
C: 24.8% Pser, 22.4% Silicate/TCP ratio
D: 26.7% Pser, 4.5% Silicate/TCP ratio All formulations could be mixed and applied within 15-60 seconds, and reached high adhesive (shear) strength within 24 hours.

Compositions comprising 25-50 wt % of phosphorylated amino acid and wherein weight ratio between the silicate compound and the α-TCP is around 1:0.8-4 have shown to work well for both soft and hard tissue. This could be very interesting when a soft tissue is to be glued or adhered to a hard tissue, for example a tendon to a bone, or a ligament to bone.

Figure 5A:
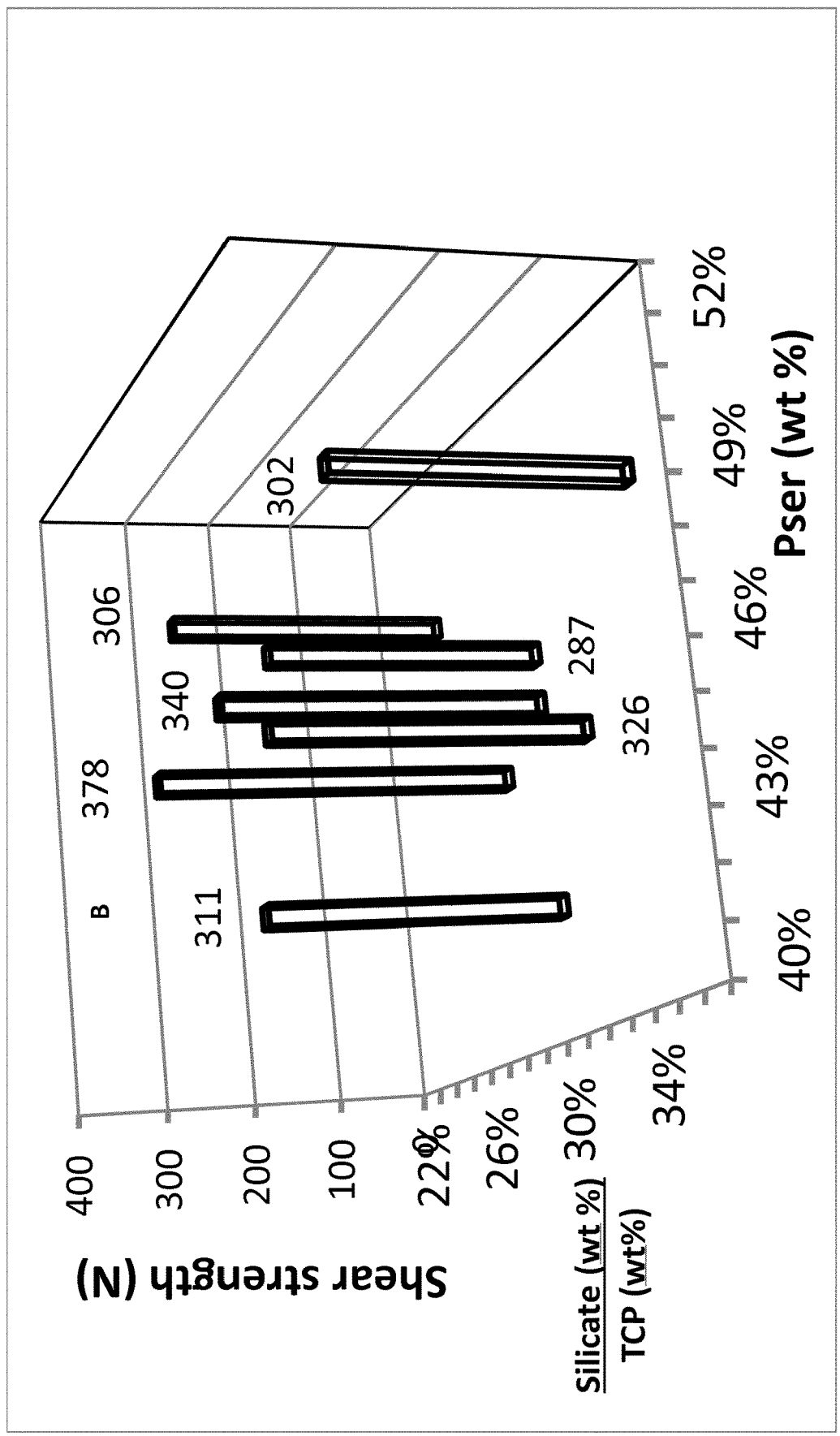
FIGS. 5A-C. Chemical composition chart for adhesion metal-to-metal, in this case aluminium. Curing time 24 hours in phosphate buffered saline, 37° C. These blow ups show shear peak values for regions corresponding to regions B-D shown in FIG. 3 for bone-to-bone adhesion.
Figure 5B:
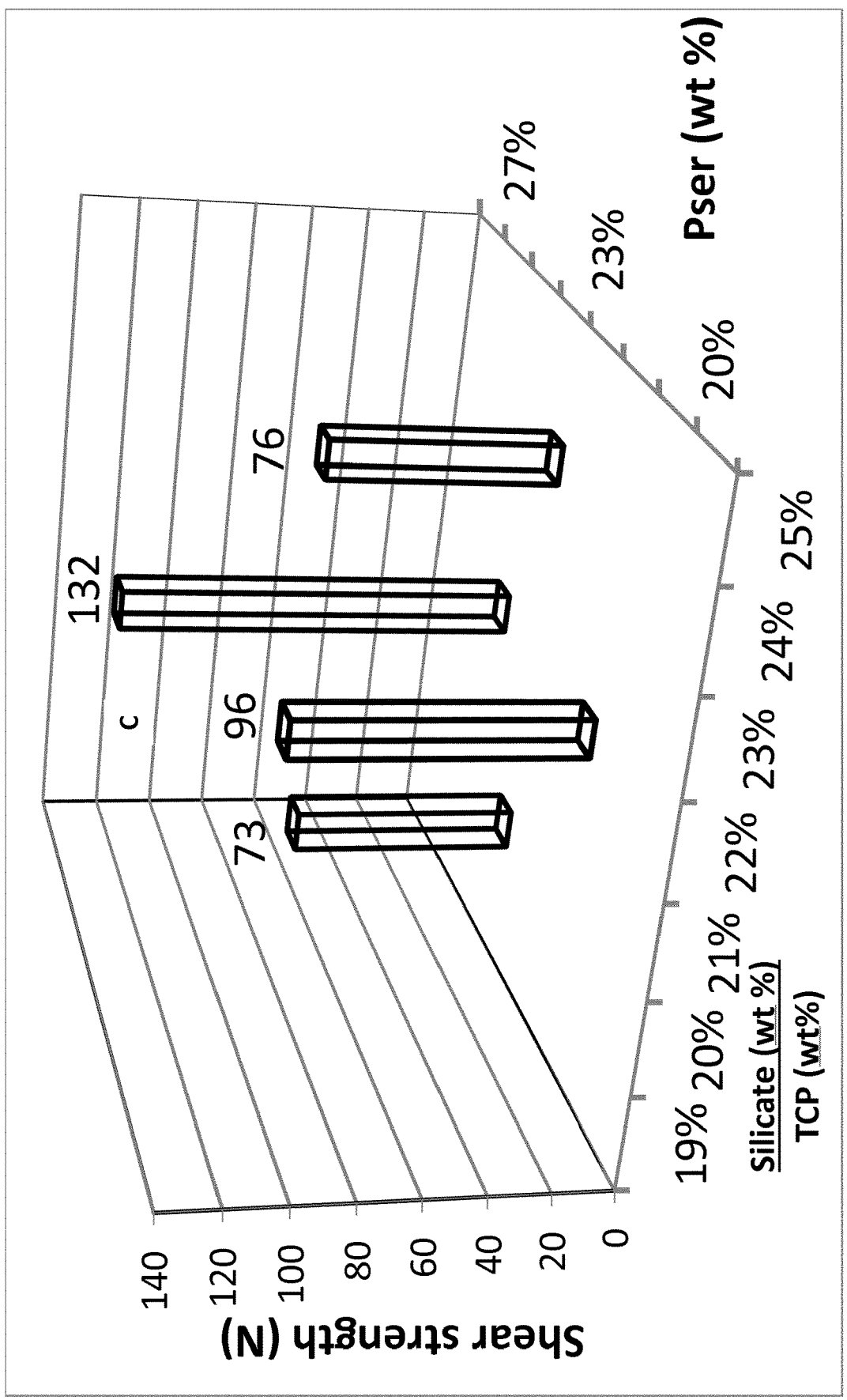
Figure 5C:
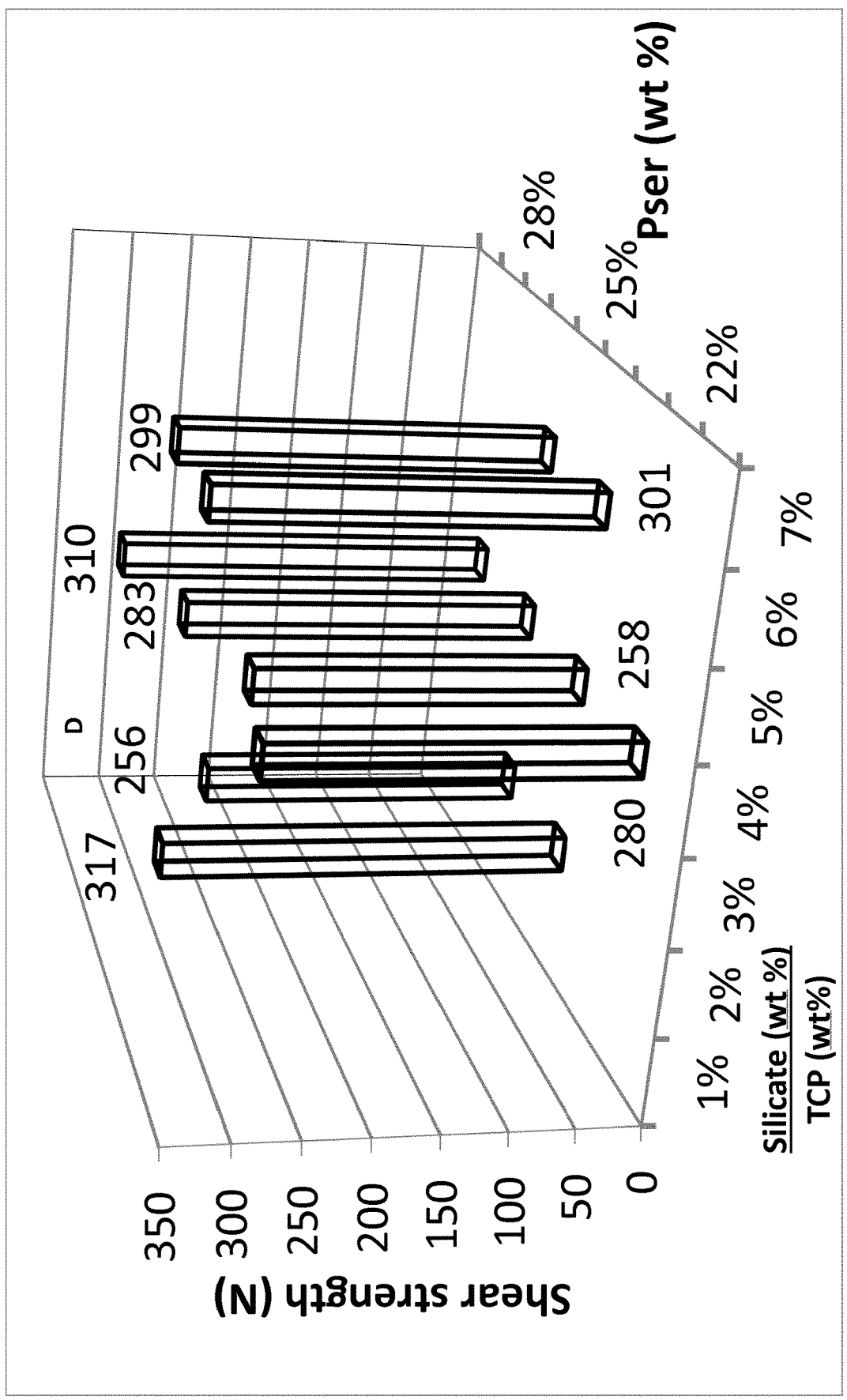

As for metal-to-metal adhesives, the best shear values were obtained for similar concentrations of the constituents as for the bone-to-bone adhesives, as can be seen in FIGS. 5A-C disclosing regions B-C. For region A the metal-to-metal tests were not completely finished, but the initial tests indicated that the same type of correlation for peak shear values and constituents could also be seen between region A of metal-to-metal and bone-to-bone.

All formulations could be mixed and applied within 15-60 seconds, and reached high adhesive (shear) strength within 1 hour.

A retardant such as sodium citrate may be added to the reaction mixture and the amount may be 1-10 wt % (solid content) or 0.8-8 wt % of the total weight of the composition. In one embodiment the amount of the retardant is 3.5-7 wt % of the solid content. The retardant may be but is not limited to sodium citrate or citric acid. Preferably, the retardant is in liquid form. It will in such a case replace the liquid, i.e. is not be part of the solid content. The total mass is then approximately 9% and below. Therefore, the retardant is never more than 10% of total mass. A retardant amount as low as 2-3% also works, though 4-6% is a preferred range.

The composition may further comprise additives such as growth factors, nutrients, anti-oxidants and so on. But the composition works without retardants and additives and in one embodiment at least 95 wt % of the solid content of the composition comprises α-TCP, phosphorylated amino acid and silicate compound, such as at least 98 wt %, or at least 99 wt %.

Preparing and Curing of the Composition

The composition is formed by mixing the solid components silicate compound, α-TCP and phosphorylated amino acid with the aqueous solution.

Preparing the composition may be done by premixing the silicate, phosphoserine (pSer) and α-TCP powders. The mixing may be done by stirring, kneading or shaking using any suitable means. The aqueous solution is then added and mixed. Formulations with higher amounts of pSer are easy to mix, while some formulations require mechanical force to get a good mixture. The mixing is done during a couple of seconds such as 10-30 seconds and may then be allowed to set for a couple of seconds, 5-120 seconds, prior application.

The curing may be done at any suitable temperature. In one embodiment the mixing is done at room temperature or below, 10-25° C., and kept at 25° C. or lower, such as 10-20° C. After applying the composition the curing temperature is preferably increased to 37° C. or higher.

Curing of the composition will occur when mixing the solid components silicate compound, α-TCP and phosphorylated amino acid with the aqueous solution. The curing reaction will lead to the formation of a thick paste and ultimately a solid cement.

The composition according to the present invention provides improved mechanical strength and may have a shear strength to skin of at least 20 kPa, or at least 40 kPa, or at least 60 kPa, or at least 80 kPa, or at least 1000 kPa when measured after 1.5 h of curing at 100% humidity and 37° C.

The composition according to the present invention may have a shear strength to bone of at least 1.5 MPa, or at least 2 MPa, or at least 2.5 MPa, or at least 3 MPa, or at least 3.5 MPa when measured after 24 h of curing at 100% humidity and 37° C.

Applications

Figure 11:
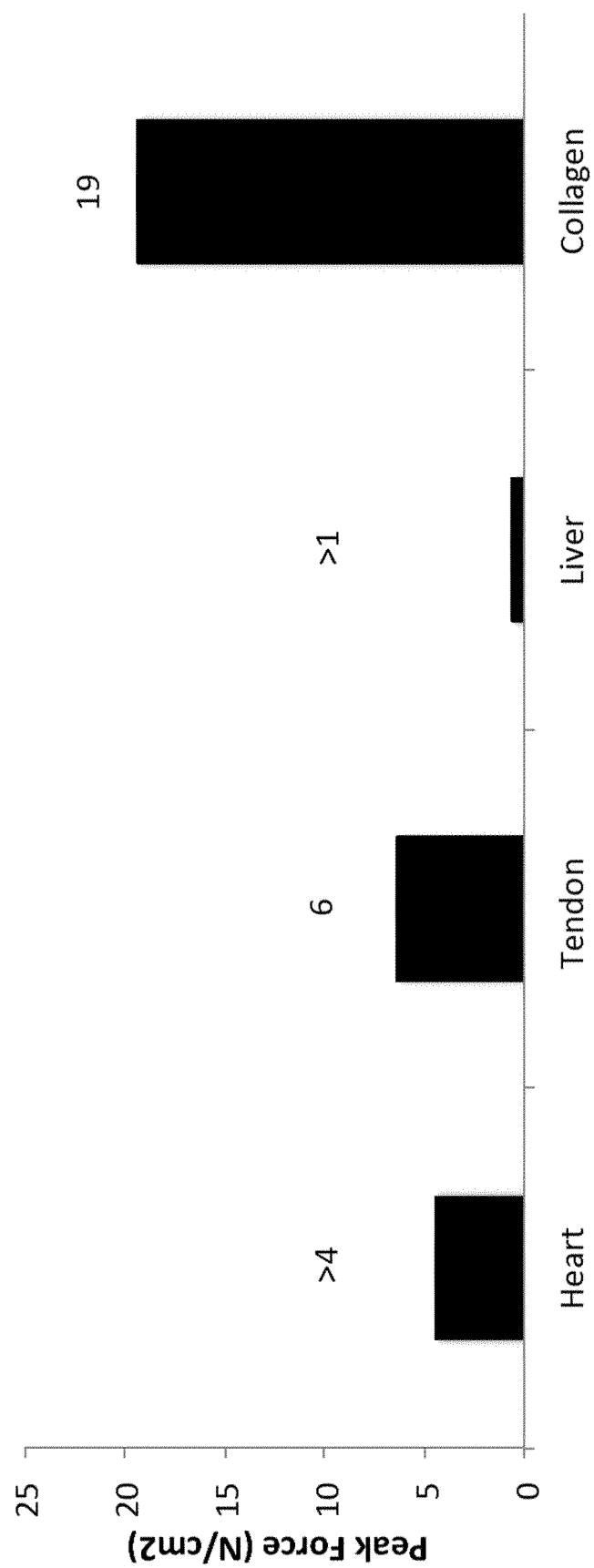
FIG. 11. Self-tissue adhesion strength (lap shear) of Portland white cement (mixture of di- and tricalcium silicates where the major elements are $SiO_2$ (24.5%), $Al_2O_3$ (2.1%) and CaO (69.1%)) (soft tissue). Lap shear strength of soft tissues (90 minute curing time at 37° C.) adhered to self tissue type. Bond strength was greater than tissue cohesive force for liver and heart, as indicated by a ">" sign, indicating that accuracy is limited by the failure strength of the tissue-to-instrument bond (tissue tears from fixation device before the adhesive bond fails). Adhesive formulation included mixed calcium silicate.

The composition according to the present invention may be used for a variety of applications. Due to the ease of applying the composition and the mechanical strength of the cured composition the composition may be used as an adhesive for biological tissue. By applying the composition to soft tissue another soft tissue or the same soft tissue may be adhered and a sufficient mechanical strength is formed between the two soft tissues. The soft tissue may be selected from but is not limited to tendon, ligament, cartilage, fascia, skin, fibrous tissue, muscle, fat, nerve, blood vessel, liver, stomach, intestines, bladder, brain, eyes, uterus, lungs, esophagus, heart, lung, kidney, spleen and glands. In one embodiment the soft tissue is selected from fascia, skin, fibrous tissue, muscle, fat, nerve, blood vessel, liver, stomach, intestines, bladder, brain, eyes, uterus, lungs, esophagus, heart, lung, kidney, spleen and glands. In one embodiment the soft tissue is cartilage or tendon. In one embodiment the soft tissue is a tissue having an extra cellular matrix, collagen and elastin. In another embodiment the soft tissue is a tissue having an epithelium. The tissue may also be a hard tissue such as bone or tooth. FIGS. 10 and 11 disclose the peak force when the present composition is used for different soft and hard tissues.

Various implants and fillers may comprise the composition according to the present invention. For example, a bone filler may comprise the composition and optionally also other biologically active materials such as growth factors. The composition may be applied to any bone void in order to fill the void, secure or anchor an implant or to stabilize a fracture. Dental implants such as a crown, bridge, denture, screw, root filler or anchoring material may also comprise the composition according to the present invention.

An implant or a scaffold may also be adhered to a tissue by using the composition according to the present invention. The implant or scaffold may be made of synthetic or biological material or a combination thereof. Synthetic materials may be metal, polymers or ceramics where the metals may be titanium, niobium or alloys of the same or aluminum oxide, stainless steel, where the polymers may be polyurethane, polyesters (e.g. polylactic acid, polyglycolic acid, polycaprolactone), polyacrylates (e.g. polymethyl methacrylate, poly(2-hydroxyethyl methacrylate)), polyethers (e.g. polyethylene glycol), polysiloxanes, hydrogels (e.g. polyvinyl alcohol) and polyvinyls (e.g. polyethylene, polypropylene, polyisbutylene, polystyrene) and where the ceramics may be calcium phosphates (e.g. hydroxyapatite, monetit, tetra calcium phosphate), metal oxides (e.g. aluminum oxides, zirconium oxides, titanium oxides) or bioglass. Biological materials may be but is not limited to collagen, hyaluronic acid, chitosan, cells, tissue, decellularized tissue, platelet rich plasma, Matrigel®, demineralized bone, fibrin, cellulose, synthetic or natural silk etc. The material may be in the shape of particles, fibres or a solid surface.

During the healing process after treating damaged tissue the tissue or the scar lacks the sufficient mechanical strength and the repaired tissue may leak body fluids. The present invention may be used to further strengthen the tissue during healing or scar formation and may even be used to seal the tissue in order to minimize leakage of body fluids. For example in combination with sutures the present composition may be added to the tissue section to be sutured together in order to provide further strength and sealing.

Figure 6:
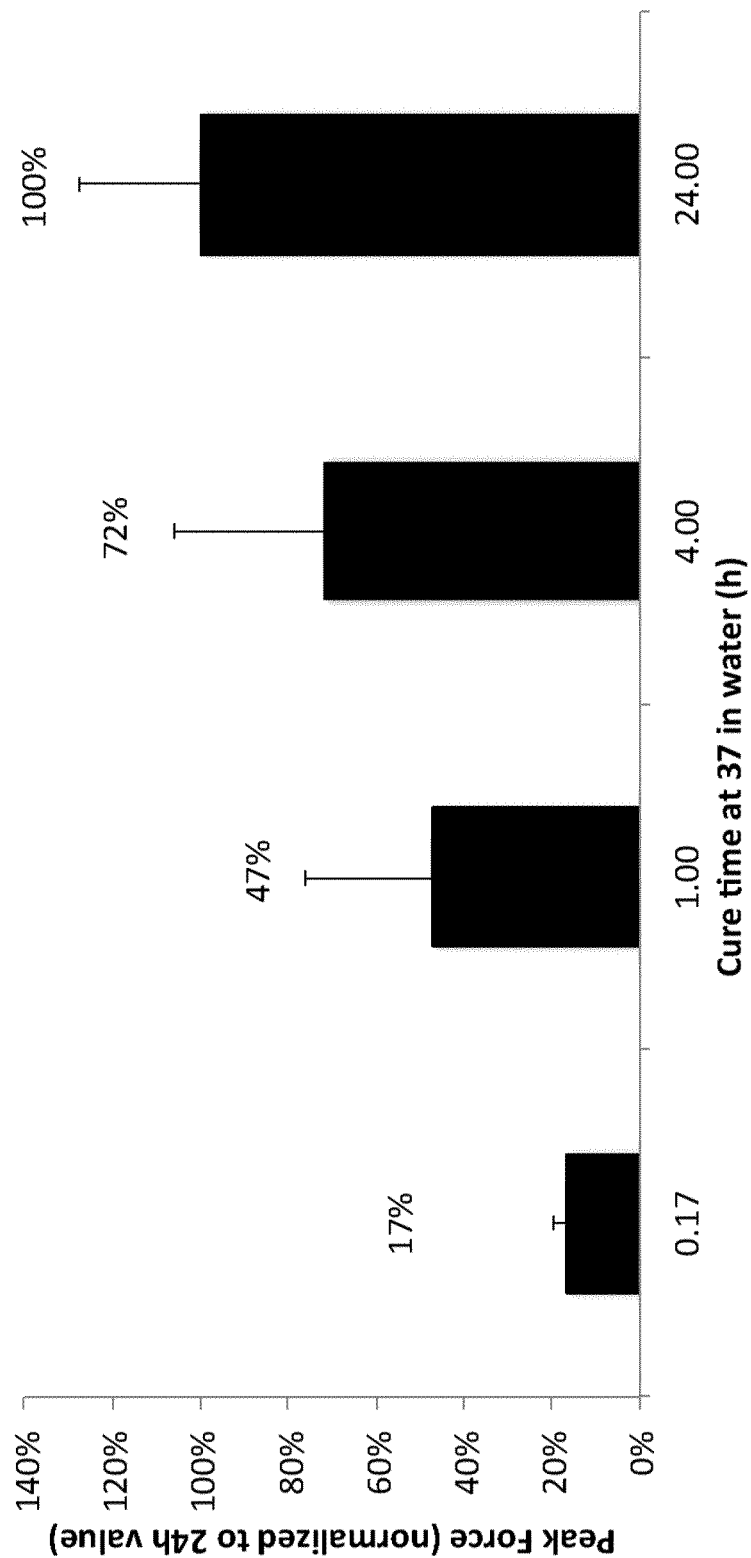
FIG. 6. Curing time for mixed silicate formulation A (25 wt % Pser, 58 wt % aTCP and 17 wt % Portland grey cement (solid content %) with 17% liquid (total wt %)). Cortical shear curing time (cured in distilled water at 21° C.), force normalized to the strength at 24 hours.

Adhering of a first tissue to a second surface may be done by applying the tissue adhesive or the composition according to the present invention to the first tissue. This may for example be two or more tissues or a tissue to a surface such as an implant or scaffold. The composition may also be applied to the second surface as well. The adhesive may be left for a suitable period of time before bringing the two or more tissues or surfaces into contact with each other. The time is dependent on content of the adhesive and the curing time and also on the tissues or materials but non-limiting examples are 10 seconds or longer, or 30 seconds or longer, or 1 minute or longer, or 5 minutes or longer. In one embodiment the composition is left for 20 seconds to 60 seconds before bring the two or more tissues or surface into contact with each other. The surfaces are then brought into contact with each other and if necessary pressure may be applied. The pressure is applied depending on the tissue/material and the cure time of the composition but non-limiting examples are 10 seconds or longer, or 30 seconds or longer, or 1 minute or longer, or 5 minutes or longer. In one embodiment a pressure is applied for 1-3 minutes. In order to cure the composition faster energy may be applied to the composition or to the part of the tissue to which the composition have been applied. This may be done by applying UV, heat or radiation of any suitable type for a couple of seconds up to minutes. The adhesive or the composition is then left to cure to the final cured composition. The adhesive may be fully cured after 5 minutes up to 48 hours depending on the composition and the tissue or surface. FIGS. 5 and 6 show the peak force after different curing times.

The curing time is dependent on the ratios of the inherent components however due to that the composition starts to cure when mixed the composition is mixed together at a suitable time prior to use or application. In certain applications the composition should cure rapidly after application of the composition and in other applications a slower curing is wanted. The present invention facilitates tailoring of the curing time so that the user may prepare the composition on beforehand without having a fully cured composition when it is time to apply it or prepare it to obtain a composition that is still shapeable or to prepare a composition that cures almost instantly.

The method may be performed in vivo or in vitro but some of the steps may be done in vitro followed by steps done in vivo. For example pieces of bone may be adhered to each other using the composition or adhesive according to the present invention and cured in vitro before put in place in vivo. Injuries that require replacement of large pieces of bone (>2-20 mm) are unable to heal without intervention. Such large pieces of bone cannot currently be grown for implantation because oxygen and nutrients cannot penetrate deeper than 500 um-2 mm. One example of a solution to this problem is to grow multiple smaller pieces of bone and to adhere them together (in vitro or ex vivo), immediately prior to implantation in vivo by using the composition according to the present invention. Tissue engineered constructs, such as bone scaffolds, are often limited by size because vascular channels that allow oxygen and nutrients to properly penetrate large constructs cannot be printed, carved or created easily. One example of a solution is to print smaller modules or pieces of a large construct and to grow them individually before assembling into increasingly larger constructs, in vitro, via an adhesive according to the present invention. The final construct can then be implanted, in vivo, following a suitable acclimation and growth period in vitro.

Screw augmentation is employed when weakened or injured bone requires reinforcement, often with metal plates, wires, or other orthopaedic fixation devices. A significant unresolved challenge in the field is fixation of poor quality bone. A bone adhesive could increase the screw-bone bond strength, especially in weak bone, over currently available augmentation agents (poly-methyl-methacrylate (PMMA) derivatives and calcium phosphates) because neither is successful at forming strong bonds with bone.

Figure 14A:
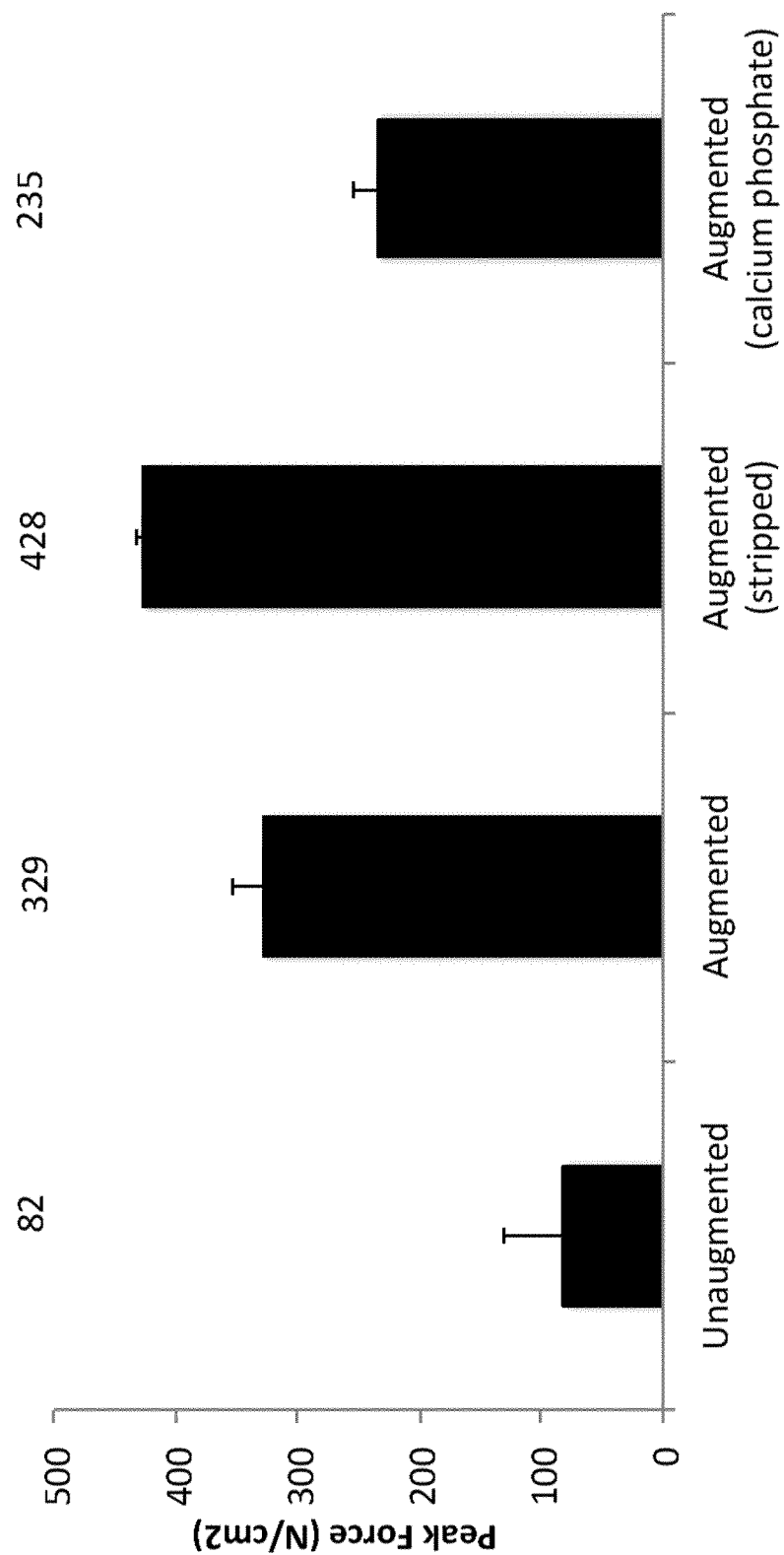
FIG. 14A. Pull-out force of Portland grey cement and screws in cancellous bone augmentation models (hard tissue). Pullout force of orthopedic screws from augmented cancellous bone (cured at 21° C., 100% humidity, 24 hours).

FIG. 14A demonstrates that the mixed silicate adhesive can increase the screw pull-out force compared to untreated bone (non-augmented), calcium phosphate treated bone (augmented), and can even increase the pullout force in a "stripped" model, where the screw has been re-inserted after being pulled out. This second model demonstrates that even when the augmentation hole has been completely "stripped" of the contact area between screw and bone that normally provides the resistance to pull-out, pull-out resistance can be restored by the adhesive.

Tetra calcium phosphates react too quickly, especially in large quantities (above 1 gram), to apply easily. In an actual operation room a physician will require a minimum of 2-5 minutes from start to application of adhesive, to allow for difficulty in mixing, surgical complications, etc.

The working time can be broken into three phases: The mixing and tacky phase, the dough phase and the final cured phase. During the mixing and tacky phase the mixture is easily mixed and flows with minor resistance. The preferred application period is near the end of the tacky phase and beginning of the dough phase. The dough phase is characterized by an increase in cohesion and decrease in adhesion. During the dough phase adhered tissue can be easily rearranged, aligned or even separated and reattached with minor effect on the final bond strength. However, during the dough phase application of the thickened and more cohesive mixture can be more difficult, thus the tacky phase is the preferred application period, while the dough phase is the preferred time for rearrangement. Finally, during the final cure phase the adhesive no longer moves easily, if at all, and revisions may significantly affect final bond strength.

FIG. 15 indicates that high concentrations of sodium citrate, but not citric acid, are capable of extending the tacky, dough and cure time of the mixed silicate formulation. When sodium citrate is mixed into the liquid, between 5% and 50 wt % such as 20-33 wt %, the tacky phase is lengthened. This extension allows the end user 3-4-fold as much time during the tacky period (from 40 seconds up to 3 minutes) and up to 7-fold more time during the dough phase (from 1 minute up to 7 minutes).

Kit for Preparing the Composition

A kit comprising the different components of the composition may be used to prepare the present composition. The kit may comprise at least two containers where the containers may be any suitable type of container such as a bowl, bag, dish, plate, beaker, flask, tin, cup or bottle and may be of any size and shape. Any one container in the kit can contain any of an aqueous solution, the phosphorylated amino acid, the silicate compound or the α-TCP or a combination thereof, with the proviso that both the phosphorylated amino acid and the α-TCP cannot be present in the same container as the aqueous solution. In other words one container may comprise the aqueous solution while a second or additional container may comprise the solid components (the phosphorylated amino acid, the silicate compound and the α-TCP), or one container may comprise the aqueous solution and one of the solid components and the second container comprises the other two solid components, or one container comprises the aqueous solution and one of the solid components and the second container comprises the aqueous solution and the other two components (with the proviso that the other two components are not α-TCP and the phosphorylated amino acid). The silicate compound may be in the form of two or more reactants that may react to form the silicate compound. The two or more reactants may be in the same compartment or may be in separate compartments. In one embodiment the kit comprises three or more containers. The amount of aqueous solution, phosphorylated amino acid, silicate compound and α-TCP in the containers is such that when mixed the composition according to the present invention.

The kit may also be in form of a syringe having at least two compartments. The compartments in the syringe can contain any of an aqueous solution, the phosphorylated amino acid, the silicate compound or the α-TCP or a combination thereof. However both the phosphorylated amino acid and the α-TCP cannot be present in the same compartment as the aqueous solution. In other words one compartment may comprise the aqueous solution while a second or additional compartment may comprise the solid components (the phosphorylated amino acid, the silicate compound and the α-TCP), or one compartment may comprise the aqueous solution and one of the solid components and the second compartment comprises the other two solid components, or one compartment comprises the aqueous solution and one of the solid components and the second compartment comprises the aqueous solution and the other two components (with the proviso that the other two components are not the α-TCP and the phosphorylated amino acid). In one embodiment the kit comprises three or more compartments. The amount of aqueous solution, phosphorylated amino acid, silicate compound and α-TCP in the compartments is such that when mixed the composition according to the present invention.

The syringe further comprises a mixing device that is configured to mix the components of the compartments during application of the components. The mixing device may be arranged at the tip of the syringe or within the compartments.

EXAMPLES

Example 1

Compositions were prepared by premixing the silicate compound (0.0216 g, Portland grey cement containing dicalcium and tricalcium silicate, with 90% of particle size distribution below 50 μm), pSer (0.0318 g) and α-TCP powders (0.075 g, with 90% of particle size distribution below 75 μm) by stirring with a spatula. Distilled water (0.0266 ml, 17.5 wt % of the total weight) was then added to the premixture and mixed by stirring for 30 seconds.

The composition was spread onto a cortical cube surface (1 cm×1 cm), to approximately 0.3-1 mm thickness with a spatula, sealed with manual clips, and submerging into distilled water kept at 37 C, within 60 seconds of adding the liquid. The mechanical testing was done using a Shimadzu AGS-X machine, with trapezium liteX software, at a crosshead speed of 1 mm/minute. After testing the surface area of each cube that was covered with adhesive was measured with calipers and the recorded peak force was divided by the surface area to produce force per surface area (N/cm2).

Figure 1:
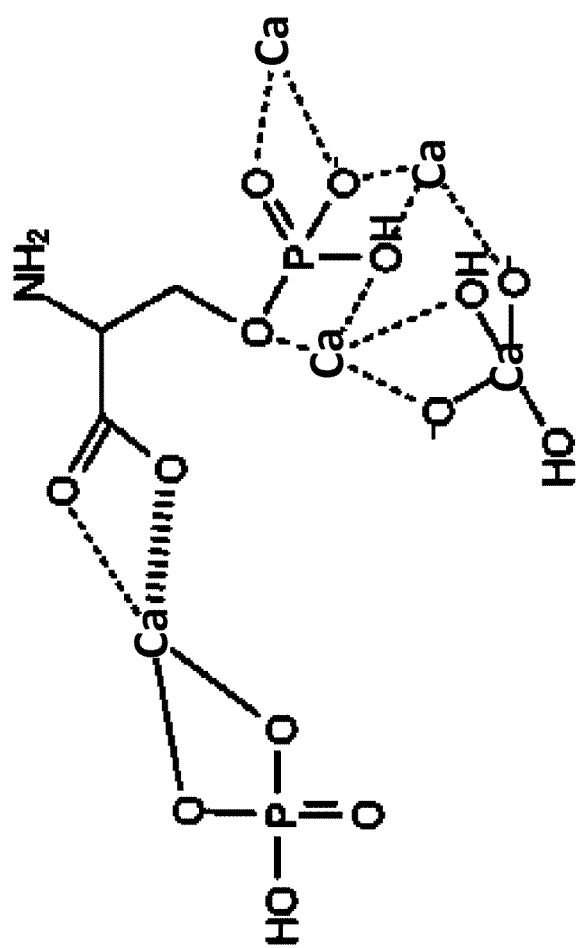
FIG. 1. Schematic view of the chemical structure of calcium-phosphoserine interaction FIG. 2. Chemical composition chart (hard tissue). Cortical shear (for bone-to-bone adhesion) after 24 hours in phosphate buffered saline, 37° C.
Figure 2:
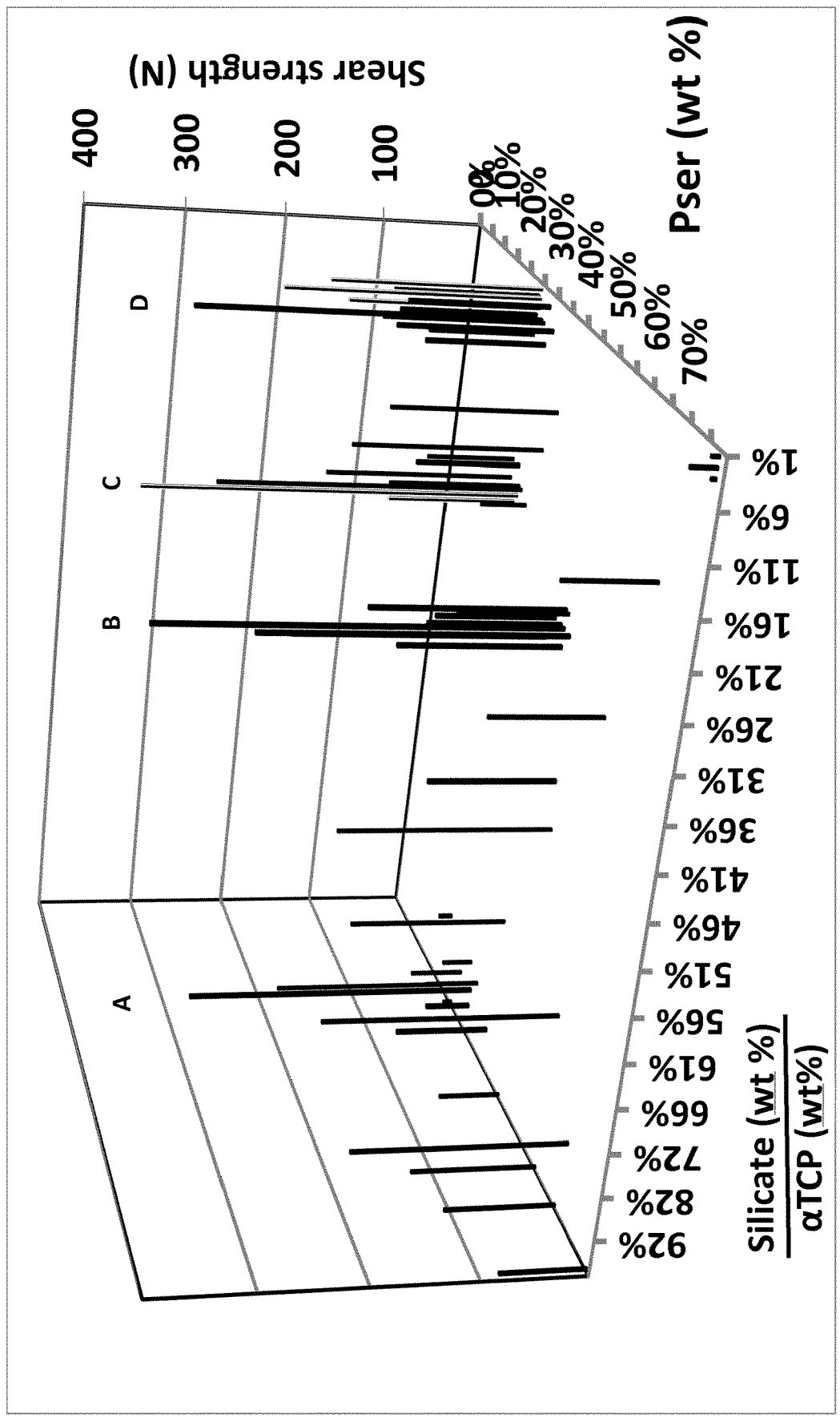
Figure 3A:
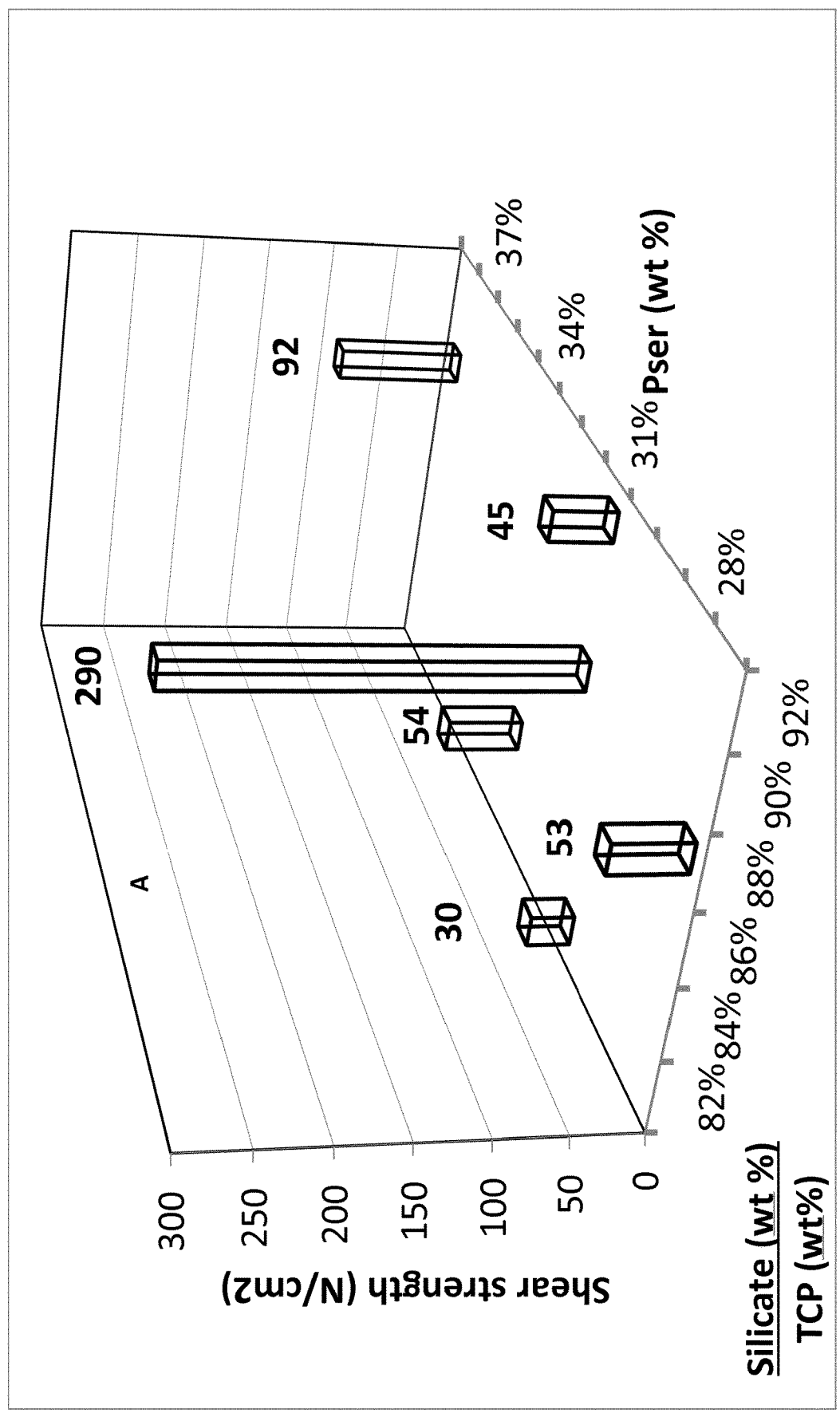
FIGS. 3A-D. Blow ups of regions A-D shown in FIG. 2 for bone-to-bone adhesion.
Figure 3B:
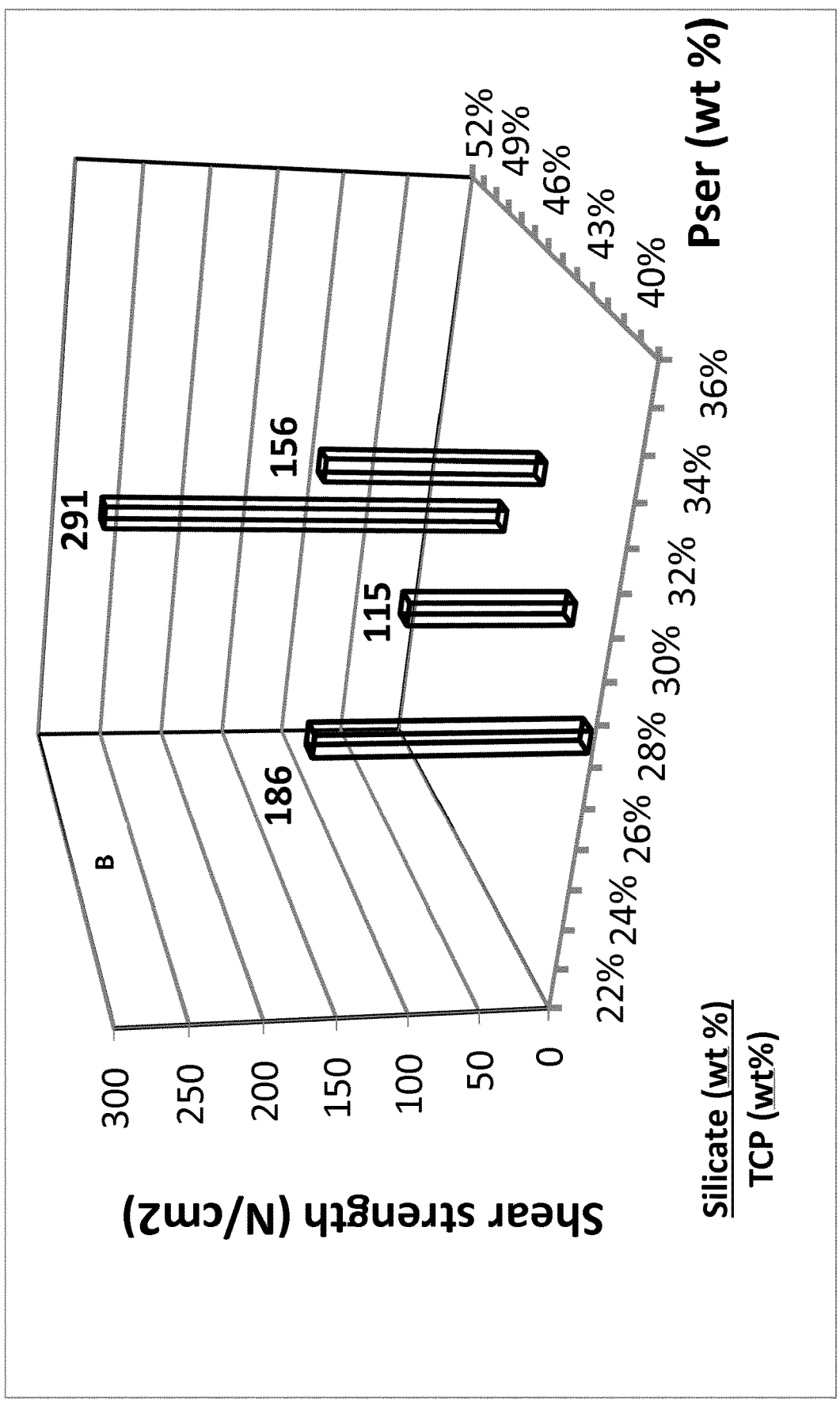
Figure 3C:
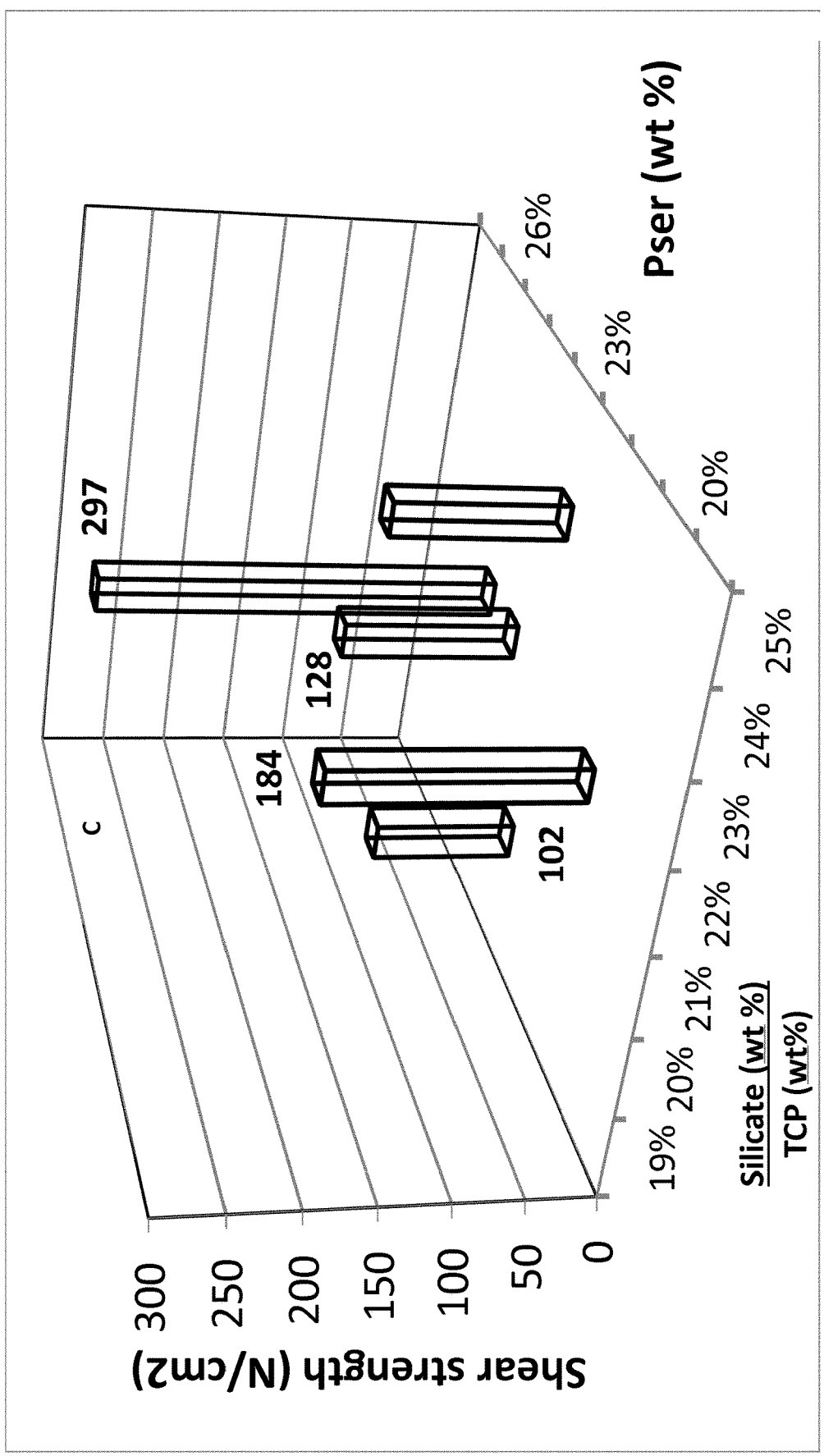
Figure 3D:
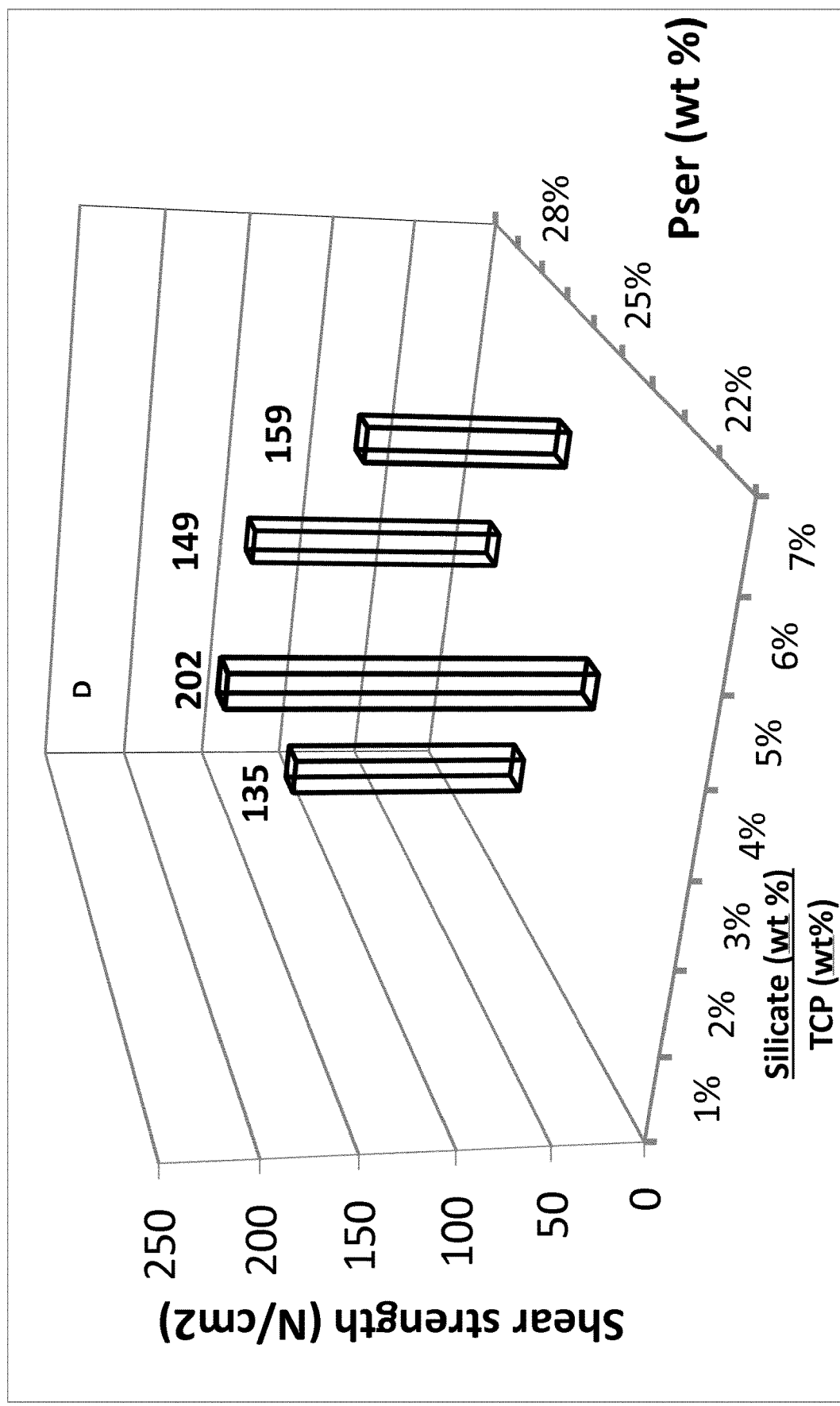

The results are disclosed in FIG. 2.

Example 2

Compositions were prepared by premixing the silicate compound (0.0228 g, Portland white cement containing dicalcium and tricalcium silicate, with 85% of particle size distribution below 50 um), pSer (0.1439 g) and α-TCP powders (0.0909 g, with 90% of particle size distribution below 75 um) by stirring with a spatula. Distilled water (0.0533 ml, 17.5 wt % of the total weight) was then added to the pre-mixture and mixed by stirring for 30 seconds.

The formulation was spread onto two strips of porcine skin (1 cm×1.5 cm) with a spatula, sealed with manual clips, and put into a sealed container that maintained 100% relative humidity, within 60 seconds of adding the liquid. Each sample was cured for 90 minutes. The mechanical testing was done using a Shimadzu AGS-X machine, with trapezium liteX software, at a crosshead speed of 5 mm/minute. After testing the surface area of each skin strip that was covered with adhesive was measured with calipers and the recorded peak force was divided by the surface area to produce force per surface area (N/cm2).

The results are disclosed in FIG. 4.

Example 3

Each sample was prepared by premixing 0.0318 g phosphoserine, 0.0216 g Portland grey cement and 0.075 g α-TCP (0.1285 g in total) powder. Distilled water (17.5% wt % of total weight) was added, followed by mixing with a spatula for 30 seconds. The formulation was spread onto a cortical cube surface (1 cm×1 cm), to approximately 0.3-1 mm thickness with a spatula, sealed with manual clips, and submerging into distilled water kept at 21 C, within 60 seconds of adding the liquid. Each sample was cured for 10, 60, 240, or 14,400 minutes.

The results are disclosed in FIG. 6.

Example 4

Each sample was prepared by premixing 0.1439 g phosphoserine, 0.0228 g Portland grey cement and 0.0909 g α-TCP (0.257 g in total) powder. Distilled water (17.5% wt % of total weight) was added, followed by mixing with a spatula for 30 seconds. The formulation was spread onto two strips of porcine skin (1 cm×1.5 cm) with a spatula, sealed with manual clips, and put into a sealed container that maintained 100% relative humidity, within 60 seconds of adding the liquid. Each sample was cured for 10, 90 or 240 minutes.

The results are disclosed in FIG. 7.

Example 5

Each sample was prepared by premixing 0.0318 g phosphoserine, 0.0216 g Portland grey cement and 0.075 g α-TCP (0.1285 g in total) powder. Distilled water (17.5%, 29.3% or 45.3% wt % of total weight) was added, followed by mixing with a spatula for 30 seconds. The formulation was spread onto a cortical cube surface (1 cm×1 cm), to approximately 0.3-1 mm thickness with a spatula, sealed with manual clips, and submerging into distilled water kept at 21 C, within 60 seconds of adding the liquid. Each sample was cured for 24 hours.

The results are disclosed in FIG. 8.

Example 6

Each sample was prepared by premixing 0.1439 g phosphoserine, 0.0228 g Portland grey cement and 0.0909 g α-TCP (0.257 g in total) powder. Distilled water (17.5%, 29.3% or 45.3% wt % of total weight) was added, followed by mixing with a spatula for 30 seconds. The formulation was spread onto two strips of porcine skin (1 cm×1.5 cm) with a spatula, sealed with manual clips, and put into a sealed container that maintained 100% relative humidity, within 60 seconds of adding the liquid. Each sample was cured for 90 minutes at 21 C.

Figure 9:
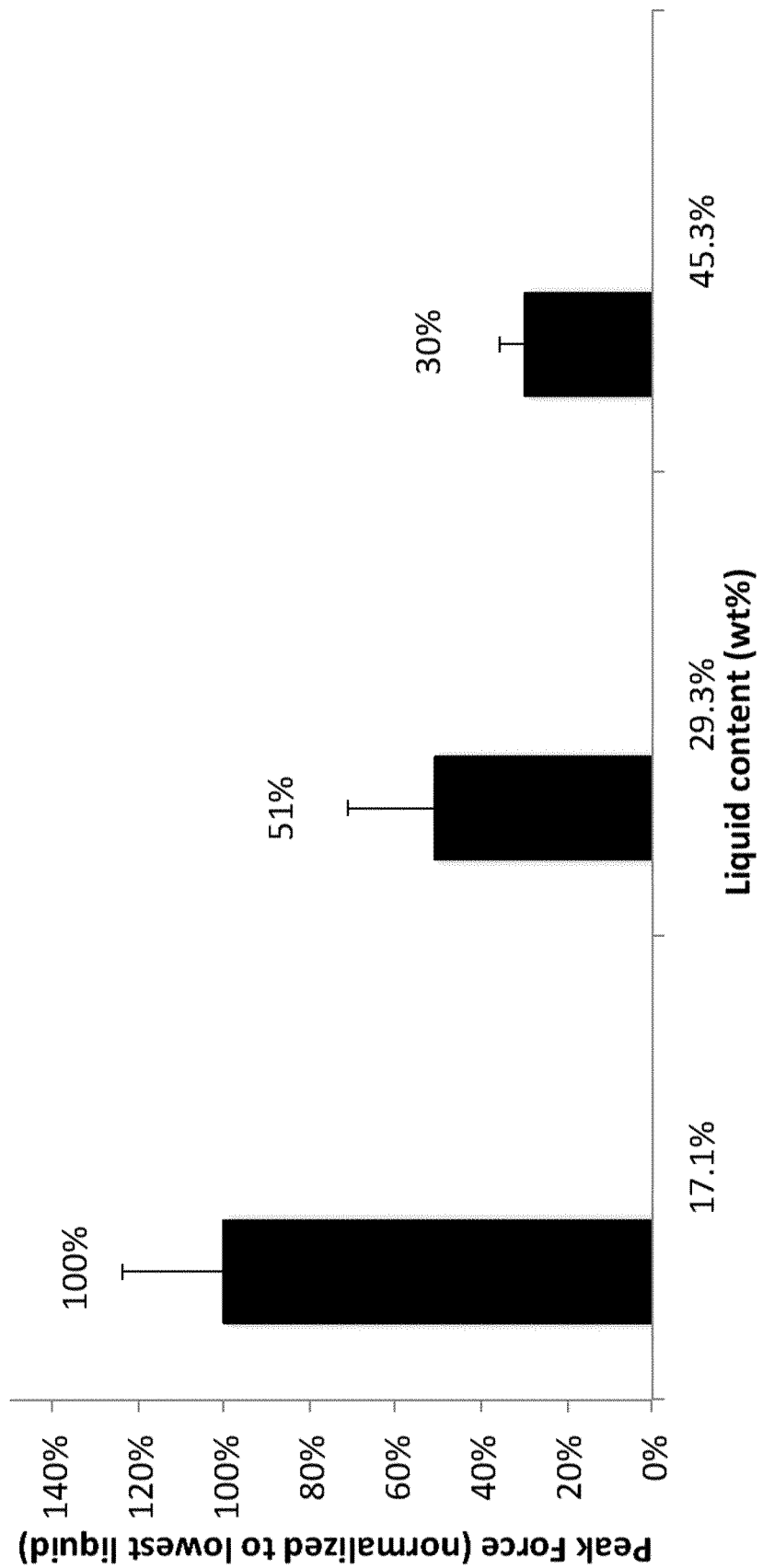
FIG. 9. Adhesive strength by water content, Portland grey cement (soft tissue). Skin shear strength with increasing water content (cured in 100% humidity at 21° C.), force normalized to the strength at lowest water content.

The results are disclosed in FIG. 9.

Example 7

Each sample was prepared by premixing 0.0318 g phosphoserine, 0.0216 g Portland grey cement and 0.075 g α-TCP (0.1285 g in total) powder. The Portland grey cement portion was entirely replaced with either dicalcium silicate or tricalcium silicate for subsequent samples. Distilled water (17.5% wt % of total weight) was added, followed by mixing with a spatula for 30 seconds. The formulation was spread onto a cortical cube surface (1 cm×1 cm), to approximately 0.3-1 mm thickness with a spatula, sealed with manual clips, and submerging into distilled water kept at 21 C, within 60 seconds of adding the liquid. Each sample was cured for 24 hours.

The results are disclosed in FIG. 10.

Example 8

Each sample was prepared by premixing 0.1439 g phosphoserine, 0.0228 g Portland grey cement and 0.0909 g α-TCP (0.257 g in total) powder. Distilled water (17.5% wt % of total weight) was added, followed by mixing with a spatula for 30 seconds. The formulation was spread onto two strips of heart, tendon, liver, or dried collagen strips (1 cm×1.5 cm) with a spatula, and put into a sealed container that maintained 100% relative humidity, within 60 seconds of adding the liquid. Each sample was cured for 90 minutes at 37 C.

The results are disclosed in FIG. 11.

Example 9

Each sample was prepared by premixing 0.0318 g phosphoserine, 0.0216 g Portland grey cement and 0.075 g α-TCP (0.1285 g in total) powder. Distilled water (17.5% wt % of total weight) was added, followed by mixing with a spatula for 30 seconds. The formulation was spread onto a cortical cube surface (1 cm×1 cm), to approximately 0.3-1 mm thickness with a spatula, sealed with manual clips, and put into a sealed container that maintained 100% relative humidity at 21 C, within 60 seconds of adding the liquid. Cartilage samples were prepared by premixing 0.636 g phosphoserine, 0.432 g Portland grey cement and 1.5 g α-TCP powder. Distilled water (17.5% wt % of total weight) was added, followed by mixing with a spatula for 30 seconds. The adhesive was poured into a square mold (1 cm×1 cm×0.5 cm) and the cartilage face was pressed into the adhesive. Each sample was cured for 24 hours.

Figure 12:
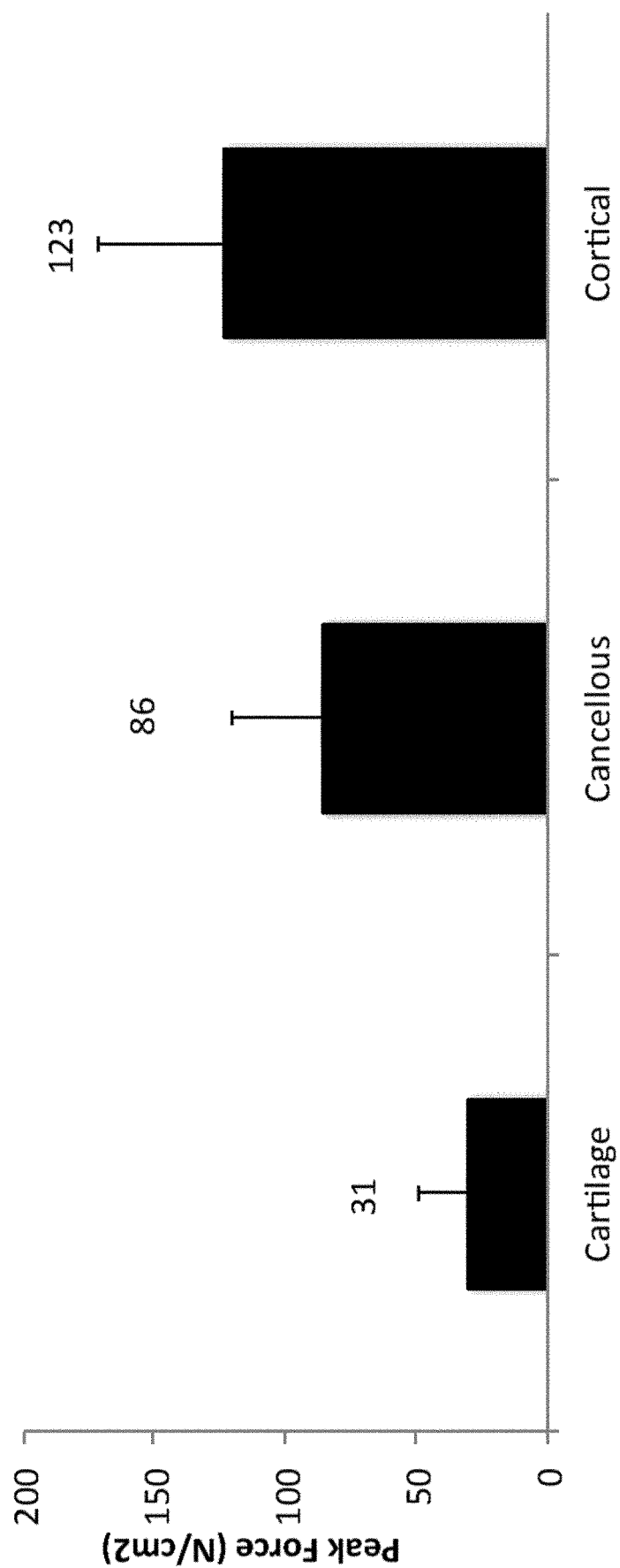
FIG. 12. Self-tissue adhesion strength (shear) of Portland grey cement (hard tissue). Hard tissue shear strength (24 hours, 100% humidity, 21° C.) with mixed calcium silicate.

The results are disclosed in FIG. 12.

Example 10

Each sample was prepared by premixing 0.0318 g phosphoserine, 0.0216 g Portland grey cement and 0.075 g α-TCP (0.1285 g in total) powder. Distilled water or tap water (17.5% wt % of total weight) was added, followed by mixing with a spatula for 30 seconds. The formulation was spread onto a cortical cube surface (1 cm×1 cm), to approximately 0.3-1 mm thickness with a spatula, sealed with manual clips, and submerging into distilled water kept at 21 C, within 60 seconds of adding the liquid. Each sample was cured for 24 hours.

Figure 13:
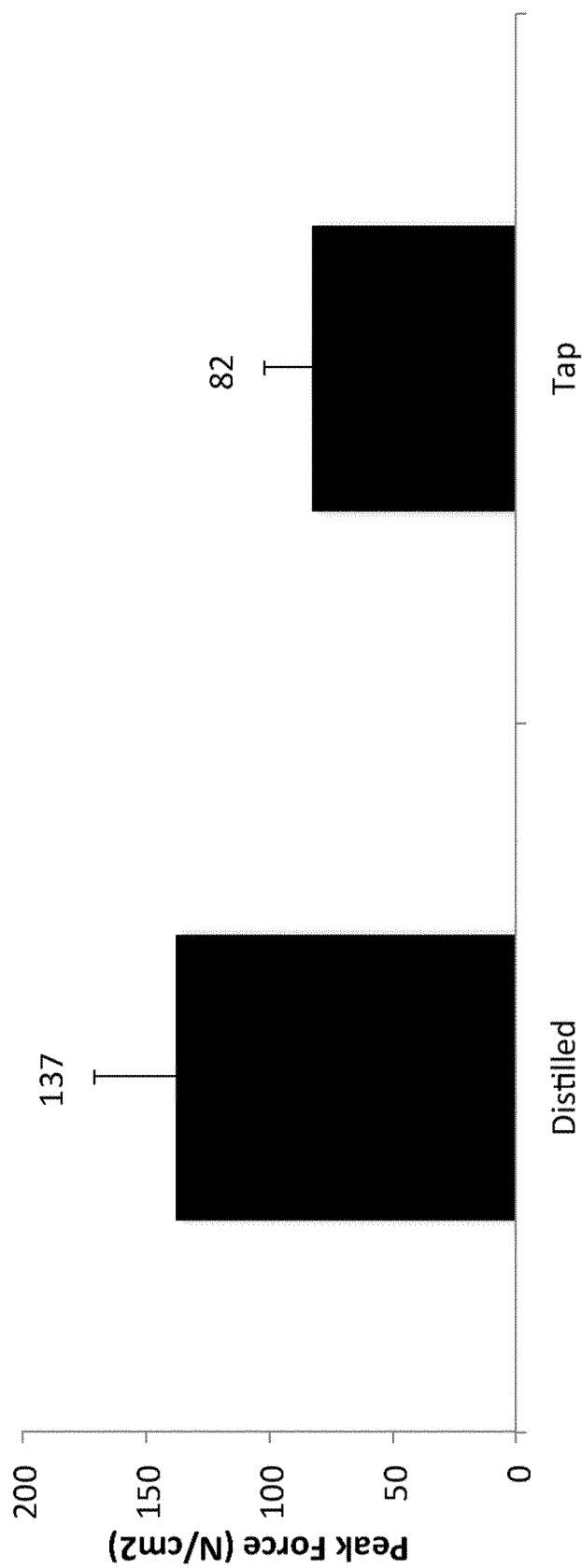
FIG. 13. Adhesion (shear) strength by liquid/solvent type of Portland grey cement (hard tissue). Effect of liquid type on cure strength of cortical bone (shear test, mixed silicate formulation, 24 hour cure in distilled water at 21° C.).

The results are disclosed in FIG. 13.

Example 11

Each sample was prepared by premixing 0.636 g phosphoserine, 0.432 g Portland grey cement and 1.5 g α-TCP powder in a 5 mL syringe. A predissolved solution of sodium citrate in distilled water (liquid is 17.5% wt % of total weight, sodium citrate 3.4% wt % of total weight) was added, followed by mixing with a spatula for 20 seconds. The formulation was injected into pre-drilled holes (6 mm diameter, 10 mm depth) in cancellous bone and an HB6.0 cancellous bone screw was inserted into the hole to a depth of 5 mm. For non-augmented samples an identical procedure was used, without the injection of adhesive. For stripped samples, non-augmented samples were tested to failure, then the sample was augmented as described above, followed by screw insertion and re-testing of pull-out force. Samples were put into a sealed container that maintained 100% relative humidity at 21 C, within 60 seconds of adding the liquid. Each sample was cured for 24 hours.

The results are disclosed in FIG. 14A.

Example 12

Each sample was prepared by premixing 0.636 g phosphoserine, 0.432 g Portland grey cement and 1.5 g α-TCP powder. A predissolved solution of sodium citrate in distilled water (liquid is 17.5% wt % of total weight, sodium citrate 3.4% wt % of total weight) was added, followed by mixing with a spatula for 20 seconds. The formulation was manually extruded into a 3 mm gap between a cancellous bone cube and a cylindrical plug that had been drilled out previously with a 2 cm crown drill. Samples were put into a sealed container that maintained 100% relative humidity at 21 C, within 60 seconds of adding the liquid. Each sample was cured for 2 hours.

Figure 14B:
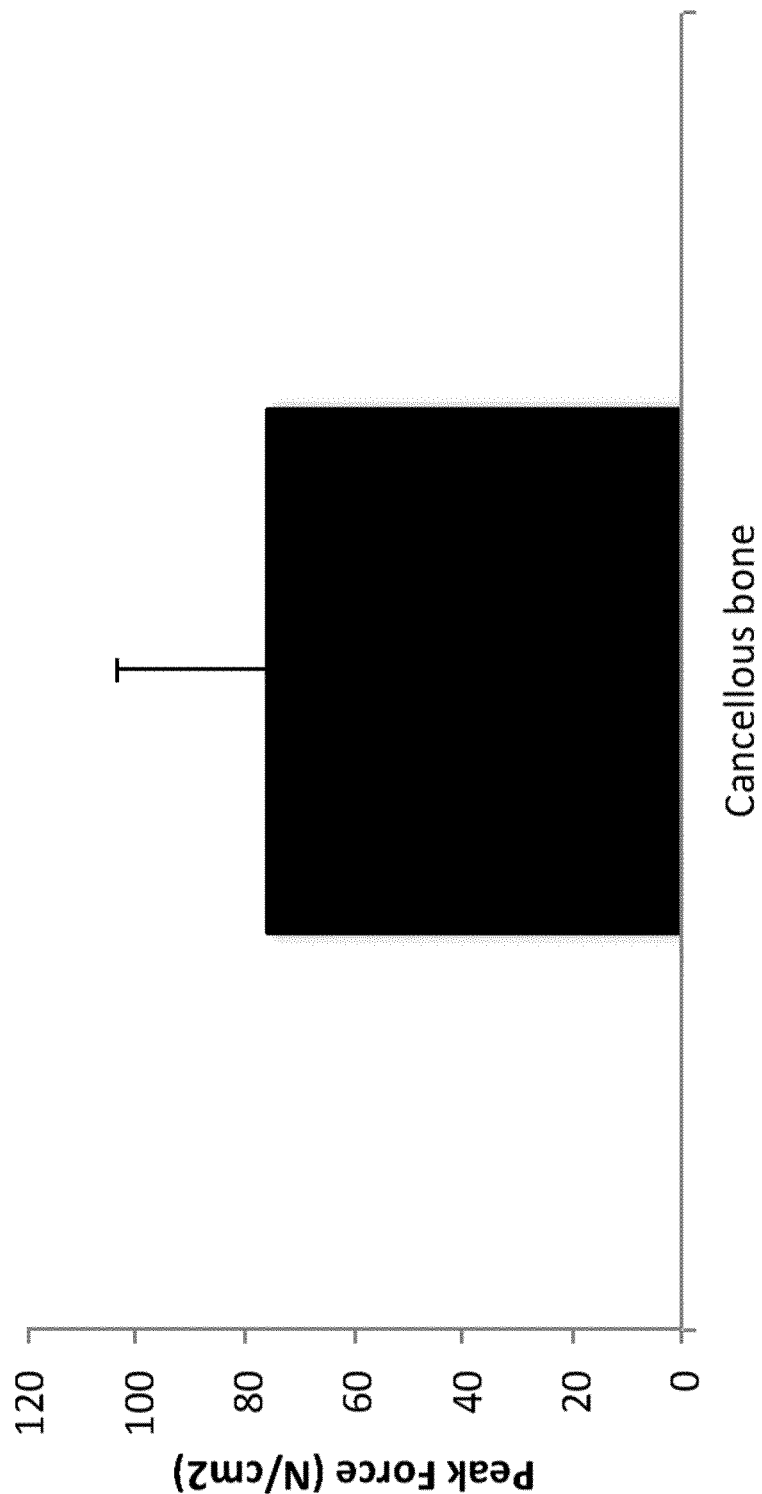
FIG. 14B. Interfacial shear (push out) force of Portland grey cement in cancellous bone plut shear (hard tissue) (cured at 21° C., 100% humidity, 2 hours).

The results are disclosed in FIG. 14B.

Example 13

Each sample was prepared by premixing 0.0318 g phosphoserine, 0.0216 g Portland grey cement and 0.075 g α-TCP (0.1285 g in total) powder. Distilled water (17.5% wt % of total weight) was added, followed by mixing with a spatula for 30 seconds. The formulation was spread onto a cortical cube surface (1 cm×1 cm) and the corresponding material surface (1 cm×1 cm) to approximately 0.1-0.6 mm thickness with a spatula, sealed with manual clips, and submerging into distilled water kept at 21 C, within 60 seconds of adding the liquid. Each sample was cured for 24 hours.

Reactivity of various ionic salts with phosphoserine, tested over the range of 20-80% phosphoserine (wt %).

Each sample was prepared by premixing 0.0318 g phosphoserine, 0.0216 g Portland grey cement and 0.075 g α-TCP (0.1285 g in total) powder. Distilled water (17.5% wt % of total weight) was added, followed by mixing with a spatula for 30 seconds. Each formulation was tested for adhesion and cohesion by visual observation of the presence or absence of a tacky phase. Salts that generate a tacky phase within 10 minutes, or before hardening, were considered "reactive".

The results are disclosed in FIG. 15.

Example 14

Each sample was prepared by premixing 0.0318 g phosphoserine, 0.0216 g Portland grey cement and 0.075 g α-TCP (0.1285 g in total) powder. A premixed solution containing sodium citrate and distilled water (liquid 17.5% wt % of total weight, with sodium citrate wt % of 0%, 0.001%, 3.4%, or 5.7% of total weight) was added, followed by mixing with a spatula for 10 minutes. The tacky phase was defined as the period where the mixture appears sticky, flowable, and can be separated from the bulk by using the spatula to "draw" out fibrils. The dough phase was defined as the period where the mixture appears less sticky, is not flowable but is still easily mixed with the spatula, and is difficult to draw out fibrils. The cured phase was defined as the period during which it was impossible to mix the formulation.

Figure 16:
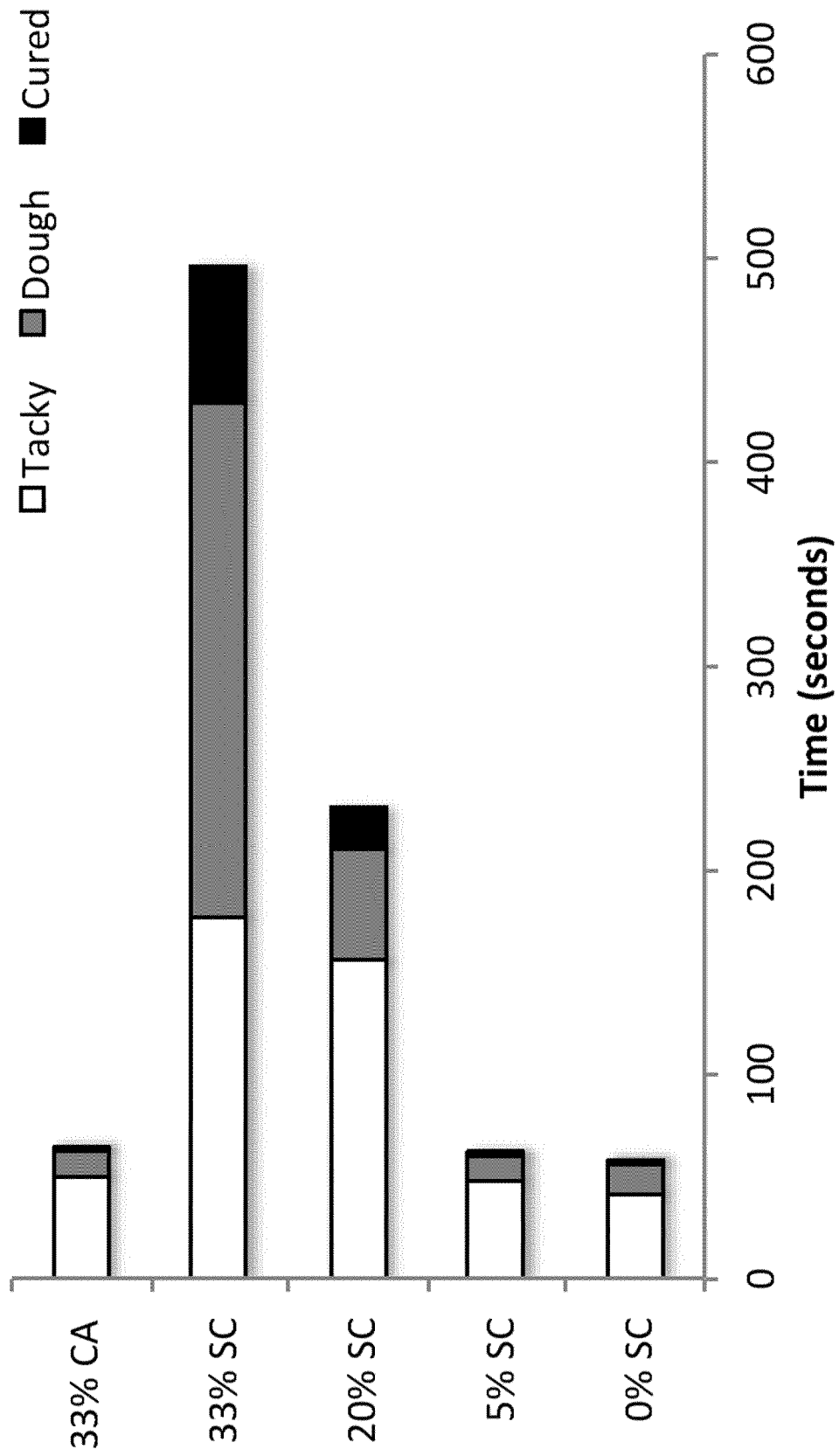
FIG. 16. Retardation of the working time of Portland grey cement by sodium citrate (SC) or citric acid (CA).

The results are disclosed in FIG. 16.

Example 15

Each powder was sieved using 25 um, 50 um, 75 um and 100 um cut-offs to separate and weigh each fraction of the powder. A Retsch AS200 sieve shaker was used, at 60 amplitude for 30 minutes, twice, to sieve each powder.

Each powder was weighed (0.01 g) and spread onto carbon tape with a spatula. An image of the particle morphology was obtained on an AS02 Zeiss 1550 SEM, using a secondary electron detector, at 4 kEV.

Figure 17:
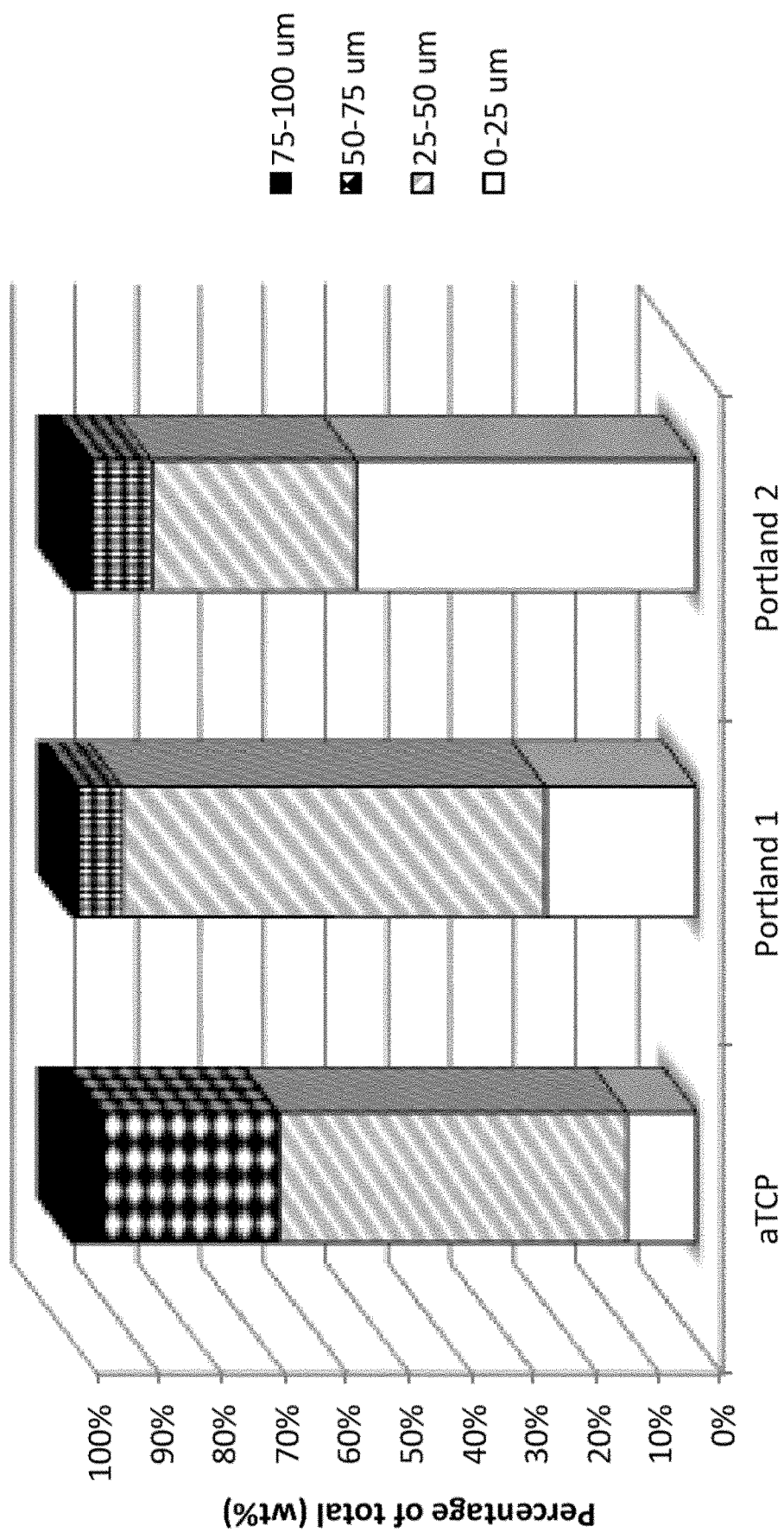
FIG. 17. Particle size distribution of the powders as determined by sieving.

The results are disclosed in FIG. 17.

Example 16

Human dermal fibroblasts (HDFn) cells were exposed to leach extracts from formulations containing silicate and tricalcium phosphate, as recommended by ISO standards 10993-5, 10993-12. Adhesive formulations, as described in table 3, were mixed, weighed and exposed to liquid after a curing time of 120 seconds. 1 mL of liquid media was added per 0.2 g of adhesive, and incubated for 24 hours at 37° C. The liquid was then centrifuged to remove debris, pH neutralized (only for "Neutral" formulations), and sterile filtered. The liquid media was diluted with 1 volume (2-fold dilution, white bars), or 3 volumes of liquid media (4-fold dilution, black bars), then exposed to HDFn cells for 24 hours. Toxicity may arise due to many factors, therefore it was necessary to distinguish between toxicity due to the chemical elements present in leach, and toxicity due to the pH of the leach. Each formulation was tested separately as obtained, or after neutralizing ("Neutral" formulations, right side of graph).

Cell viability was determined by replacing the liquid media with a 10% solution of alamar blue, in liquid media, and incubating for 1 hour. The flourescent intensity at at 560 nm was subtracted from the intensity at 590 nm, which represents the amount of alamar blue that is reduced by cellular activities, including metabolism. The amount of reduction is directly related to the number of cells and is therefore used to indicate the number of viable cells. The percentage values indicate the amount of viable cells in each treatment group, normalized to the untreated (control) group.

Figure 18:
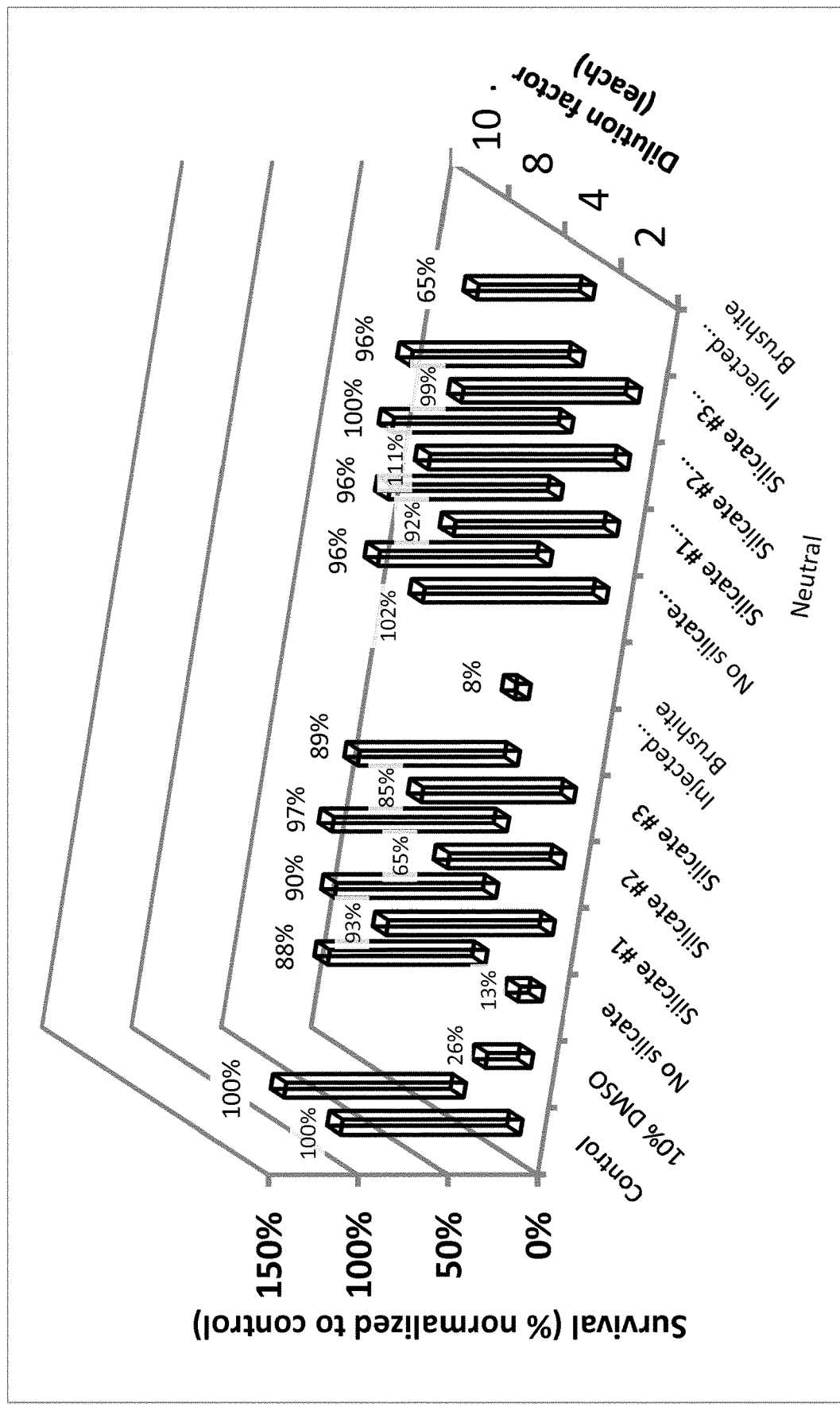
FIG. 18. Human fibroblast cell survival following exposure to leach extracts.

The results of the experiment are shown in FIG. 18, which indicates that the observed cell toxicity is due to the acidity of the set adhesive. All treatment groups were used as obtained (left bars), or after neutralizing (right bars, "Neutral"). When the concentration was held constant, but the pH neutralized, cell toxicity was abrogated.

The pH of leach from compositions mentioned above are shown in Table 1 below.

| Formula | Pser % | Shear (N/cm2) | Sil:α-TCP | pH | Survival 1:2 | Neutralized Survival 1:2 |
|---|---|---|---|---|---|---|
| 0 | 22% | 321 | 0% | 5.55 | 13% | >99%* |
| 1 | 25% | 313 | 23% | 7.60 | 93% | 92% |
| 2 | 25% | 429 | 2% | 5.62 | 65% | >99%* |
| 3 | 45% | 291 | 28% | 5.99 | 85% | 99% |

*Cell numbers increased, suggesting a slight increase in fibroblast proliferation.

Table 1 lists the physical and chemical properties of each formulation tested upon human fibroblasts. The adhesive shear strength remained high for all tested formulations, despite the disparate pH and composition (wt %) values.

Example 17

Compositions were prepared by premixing the silicate compound (0.021, 0.0216, or 0.0042 g for compositions B, C or D, Portland grey cement containing dicalcium and tricalcium silicate, with 90% of particle size distribution below 50 μm), pSer (0.0574, 0.0318, or 0.03429 g for compositions B, C or D) and α-TCP powders (0.05, 0.075, or 0.09 g for compositions B, C or D, with 90% of particle size distribution below 75 μm) by stirring with a spatula. Distilled water (0.0266 ml, 17.5 wt % of the total weight) was then added to the premixture and mixed by stirring for 30 seconds. The composition was spread onto an aluminum cube surface (1 cm×1 cm), to approximately 0.3-1 mm thickness with a spatula, sealed with manual clips, and submerging into distilled water kept at 37 C, within 60 seconds of adding the liquid.

The mechanical testing was done using a Shimadzu AGS-X machine, with trapezium liteX software, at a crosshead speed of 1 mm/minute. After testing the surface area of each cube that was covered with adhesive was measured with calipers and the recorded peak force was divided by the surface area to produce force per surface area (N/cm2).

The results are disclosed in FIGS. 5A-C, showing the results of tests with compositions B, C and D. Said compositions represent the peak shear value compositions for adhesion to metal.

Formula 1 comprises 22-28 wt % phosphorylated amino acid (phosphoserine) and 20-24 wt % silicate (silicate meaning weight ratio between silicate compound and α-TCP)

Formula 2 comprises 23-29 wt % phosphorylated amino acid (phosphoserine) and 2-6 wt % silicate.

Formula 3 comprises 40-48 wt % phosphorylated amino acid (phosphoserine) and 28-33 wt % silicate, Table 2 below lists all bone-to-bone and metal to metal adhesive compositions shown in FIGS. 3A-D and 5A-C.

| Pser (wt %) | Silicate:TCP (wt %) | Bone Shear Strength 24 hr (N/cm2) | Metal Shear Strength 1 hr (N/cm2) | Region |
|---|---|---|---|---|
| 24 | 1 | 204 | | D |
| 23 | 2 | 139 | | D |
| 24 | 2 | 247 | | D |
| 25 | 2 | | 317 | D |
| 27 | 2 | 135 | 256 | D |
| 24 | 3 | 185 | | D |
| 26 | 3 | 329 | | D |
| 23 | 4 | 132 | 280 | D |
| 25 | 4 | 202 | 258 | D |
| 27 | 4 | | 283 | D |
| 29 | 4 | 149 | 310 | D |
| 27 | 5 | | 429 | D |
| 23 | 6 | 102 | | D |
| 25 | 6 | | 301 | D |
| 27 | 6 | 115 | 299 | D |
| 22 | 20 | 87 | | C |
| 24 | 20 | 102 | 73 | C |
| 24 | 20 | 120 | | C |
| 22 | 22 | 96 | | C |
| 22 | 22 | 184 | | C |
| 25 | 22 | 128 | 313 | C |
| 26 | 22 | 297 | 132 | C |
| 28 | 23 | 45 | | C |
| 24 | 24 | 126 | 76 | C |
| 23 | 25 | 380 | | C |
| 39 | 25 | | 343 | C |
| 49 | 25 | | 306 | C |
| 54 | 25 | | 184 | C |
| 46 | 28 | 107 | 378 | B |
| 45 | 28 | 186 | | B |
| 42 | 30 | 115 | 311 | B |
| 45 | 30 | 127 | 291 | B |
| 46 | 30 | | 340 | B |
| 47 | 30 | 291 | 287 | B |
| 82 | 31 | 30 | | B |
| 45 | 32 | 156 | 326 | B |
| 88 | 32 | 290 | | B |
| 40 | 33 | 244 | | B |
| 49 | 35 | | 302 | B |
| 30 | 45 | 381 | | B |
| 49 | 45 | 122 | | B |
| 35 | 50 | | 232 | B |
| 57 | 65 | | 165 | B |
| 34 | 84 | 54 | | A |
| 28 | 88 | 53 | | A |
| 39 | 90 | 92 | | A |
| 32 | 92 | 45 | | A |

Table 1—Bone-to-bone and metal-to-metal adhesive compositions shown in FIGS. 3A-D and 5A-C, as well as their respective shear strength values. The silicate and alpha-TCP component represents the remainder of the solid content, i.e. 24 wt % phosposerine means that the silicate and alpha-TCP component represents the 76 wt % of the solid content.

The invention claimed is:

1. An aqueous composition comprising an aqueous solution, a silicate compound, α-TCP and a phosphorylated amino acid; wherein the amount of phosphorylated amino acid is 20-50 wt % of the solid content, the combined amount of silicate compound and α-TCP is 10-80 wt % of the solid content, wherein the weight ratio of the silicate compound to α-TCP is 1:1-50; wherein the silicate compound is a mixture of di- and tricalcium silicate; and wherein the composition has a shear strength to bone of at least 1.5 MPa when measured after 24 h of curing at 100% humidity and 37 C.

2. The aqueous composition according to claim 1 wherein the amount of phosphorylated amino acid is 20-30 wt % of the solid content.

3. The aqueous composition according to claim 1 wherein the amount of phosphorylated amino acid is 22-35 wt % of the solid content.

4. The aqueous composition according to claim 1 wherein the weight ratio of the silicate compound to α-TCP is 1:5-15.

5. The aqueous composition according to claim 1 wherein the phosphorylated amino acid is phosphoserine.

6. The aqueous composition according to claim 1 wherein the amount of aqueous solution is 5-20 wt % of the total weight of the composition.

7. The aqueous composition according to claim 1 wherein the composition further comprises a hydrogel.

8. A biological tissue adhesive comprising the composition according to claim 1.

9. The adhesive according to claim 8 wherein the tissue is a soft tissue.

10. The adhesive according to claim 9 wherein the soft tissue is selected from tendon, ligament, cartilage, fascia, skin, fibrous tissue, muscle, fat, nerve, blood vessel, liver, stomach, intestines, bladder, brain, eyes, uterus, lungs, esophagus, heart, lung, kidney, spleen and glands.

11. The adhesive according to claim 8 wherein the tissue is bone.

12. A bone filler comprising the composition according to claim 1.

13. A dental implant comprising the composition according to claim 1.

14. A method of adhering a first tissue to a second surface using the tissue adhesive according to claim 8 comprising:
applying the tissue adhesive according to claim 8 to the first tissue or to the second surface and optionally leave it for a suitable period of time;
bringing the first tissue and the second surface into contact with each other;
optionally applying a pressure on the first tissue and second surface for a suitable period of time; and letting the tissue adhesive cure.

15. The method according to claim 14 wherein the second surface is a second tissue and wherein the first or the second tissue is a soft tissue selected from tendon, ligament, fascia, skin, fibrous tissue, muscle, fat, nerve or blood vessel.

16. The method according to claim 14 wherein the second surface is a ceramic, metal or a polymeric material.

17. The method according to claim 14 wherein the second surface is a synthetic scaffold material selected from synthetic or natural silk, cellulose fibres, or biodegradable fibres selected from PLA, PGA, or PCL containing fibres.

18. The method according to claim 15 wherein both the first and the second tissue is a soft tissue.

19. The method according to claim 14 wherein the steps are performed in vitro.

20. A kit for preparing the composition according to claim 1 comprising at least two containers wherein any one container in the kit can contain any of an aqueous solution, the phosphorylated amino acid, the silicate compound or the α-TCP or a combination thereof, with the provision that both the phosphorylated amino acid and the α-TCP cannot be present in the same container as the aqueous solution; and wherein the amount of aqueous solution, phosphorylated amino acid, silicate compound and α-TCP in the containers is such that when mixed the composition according to claim 1 is obtained.

21. A syringe comprising at least two compartments wherein any one compartment in the syringe can contain any of an aqueous solution, the phosphorylated amino acid, the silicate compound or the α-TCP or a combination thereof, with the proviso that both the phosphorylated amino acid and the α-TCP cannot be present in the same compartment as the aqueous solution;

wherein the amount of aqueous solution, phosphorylated amino acid, silicate compound and α-TCP in the compartments is such that when mixed the composition according to claim 1 is obtained; and wherein the syringe further comprises a mixing device configured to mix the components of the at least two compartments.

22. The syringe according to claim 21 wherein any one compartment further comprises an injectable hydrogel.

23. The syringe according to claim 21 wherein any one compartment further comprises a first precursor component for a hydrogel and any second compartment further comprises a complementary precursor component for the first precursor.

\* \* \* \* \*